US012577286B2

(12) United States Patent
Hanada et al.

(10) Patent No.: US 12,577,286 B2
(45) Date of Patent: Mar. 17, 2026

(54) T CELL RECEPTORS WHICH RECOGNIZE MUTATED EGFR

(71) Applicant: The United States of America, as represented by the Secretary, Department of Health and Human Services, Bethesda, MD (US)

(72) Inventors: Kenichi Hanada, Bethesda, MD (US); Chihao Zhao, Bethesda, MD (US); Anna Pasetto, Stockholm (SE); James C. Yang, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 1168 days.

(21) Appl. No.: 17/051,860

(22) PCT Filed: May 1, 2019

(86) PCT No.: PCT/US2019/030108
§ 371 (c)(1),
(2) Date: Oct. 30, 2020

(87) PCT Pub. No.: WO2019/213195
PCT Pub. Date: Nov. 7, 2019

(65) Prior Publication Data
US 2021/0115108 A1     Apr. 22, 2021

Related U.S. Application Data

(60) Provisional application No. 62/665,234, filed on May 1, 2018.

(51) Int. Cl.
| | |
|---|---|
| *C07K 14/725* | (2006.01) |
| *A61K 40/11* | (2025.01) |
| *A61K 40/32* | (2025.01) |
| *A61K 40/42* | (2025.01) |
| *G01N 33/574* | (2006.01) |

(52) U.S. Cl.
CPC .......... *C07K 14/7051* (2013.01); *A61K 40/11* (2025.01); *A61K 40/32* (2025.01); *A61K 40/4204* (2025.01); *G01N 33/57492* (2013.01); *A61K 2239/55* (2023.05); *G01N 2333/71* (2013.01)

(58) Field of Classification Search
CPC ...................................................... A61K 35/17
See application file for complete search history.

(56) References Cited

U.S. PATENT DOCUMENTS

2015/0307585 A1     10/2015  Blankenstein et al.

FOREIGN PATENT DOCUMENTS

| | | | | | |
|---|---|---|---|---|---|
| CN | 107904289 | A | * | 4/2018 | ........... C12Q 1/6858 |
| WO | WO-2005094357 | A2 | * | 10/2005 | ............. A61P 35/00 |
| WO | WO 2009/126306 | A2 | | 10/2009 | |
| WO | WO-2016187508 | A2 | * | 11/2016 | ............. A61K 38/00 |

OTHER PUBLICATIONS

Alli et al. (PLoS One. Mar. 2, 20113; 6 (3): e18027; pp. 1-10).*
Rossjohn et al. (Annu. Rev. Immunol. 2015; 33: 169-200).*
Birnbaum et al. (Proc. Natl. Acad. Sci. USA. Dec. 9, 2014; 111 (49): 17576-81).*
Dimitri et al. (Mol. Cancer. Mar. 18, 2022; 21 (1): 78; pp. 1-13).*
Johnson et al. (Sci Transl Med., 7 (275) Feb. 2015.*
Baselga et al., "Critical Update and Emerging Trends in Epidermal Growth Factor Receptor Targeting in Cancer," *Journal of Clinical Oncology*, 23(11): 2445-2459 (2005).
Database Genseq, Database Accession No. BDK29507 (Jan. 26, 2017).
Database Genseq, Database Accession No. BDK29889 (Jan. 26, 2017).
European Patent Office, International Search Report in International Patent Application No. PCT/US2019/030108 (Jul. 10, 2019).
European Patent Office, Written Opinion in International Patent Application No. PCT/US2019/030108 (Jul. 10, 2019).
Liu et el., "Affinity-Tuned ErbB2 or EGFR Chimeric Antigen Receptor T Cells Exhibit an Increased Therapeutic Index against Tumors in Mice," *Cancer Research*, 75(17): 3596-3607 (2015).
Lu et al., "Treatment of Patients With Metastatic Cancer Using a Major Histocompatibility Complex Class II-Restricted T-Cell Receptor Targeting the Cancer Germline Antigen MAGE-A3," *Journal of Clinical Oncology*, 35(29): 3322- 3329 (2017).
Ping et al., "T-cell receptor-engineered T cells for cancer treatment: current status and future directions," *Protein & Cell*, 9(3): 254-266 (2017).
Sharma et al., "Epidermal growth factor receptor mutations in lung cancer," *Nature Reviews*, 7: 169-181 (2007).
Sidney et al., "Five HLA-DP Molecules Frequently Expressed in the Worldwide Human Population Share a Common HLA Supertypic Binding Specificity," *Journal of Immunology*, 184(5): 2492-2503, Author Manuscript (2010).
Zhou et al., "Cellular Immunotherapy for Carcinoma Using Genetically Modified EGFR-Specific T Lymphocytes," *Neoplasia*, 15(5): 544-553 (2013).
"TRA T-cell receptor alpha locus [*Homo sapiens* (human)]," Gene ID: 6955, (updated Oct. 9, 2016), Entrez Gene (ncbi.nlm.nih.gov/ gene), printed on Dec. 8, 2016.

(Continued)

*Primary Examiner* — Gary B Nickol
(74) *Attorney, Agent, or Firm* — Leydig, Voit & Mayer

(57) ABSTRACT

Disclosed is an isolated or purified T cell receptor (TCR), wherein the TCR has antigenic specificity for a mutated EGFR amino acid sequence with a E746-A750 deletion. Related polypeptides and proteins, as well as related nucleic acids, recombinant expression vectors, host cells, populations of cells, and pharmaceutical compositions are also provided. Also disclosed are methods of detecting the presence of cancer in a mammal and methods of treating or preventing cancer in a mammal.

29 Claims, 5 Drawing Sheets

Specification includes a Sequence Listing.

(56)          References Cited

OTHER PUBLICATIONS

"TRB T cell receptor beta locus [*Homo sapiens* (human)]," Gene
ID: 6957, (updated Oct. 9, 2016), Entrez Gene (ncbi.nlm.nih.gov/
gene), printed on Dec. 8, 2016.

Lee et al., "Somatic Mutations of EGFR Gene in Squamous Cell
Carcinoma of the Head and Neck", *Clinical Cancer Research*,
11(8): 2879-2882 (2005).

Murphy et al., eds., *Janeway's Immunobiology*, 7th Ed., New York:
Garland Science (2008), pp. 157-158 (Section 4-10).

Sakai et al., "Expression, intracellular localization, and mutation of
EGFR in conjunctival squamous cell carcinoma and the association
with prognosis and treatment", *PLOS One*, 15(8): e0238120, pp.
1-14 (2020).

Teng et al., "Mutations in the epidermal growth factor receptor
(EGFR) gene in triple negative breast cancer: possible implications
for targeted therapy", *Breast Cancer Research*, 13:R35, pp. 1-9
(2011).

* cited by examiner

SEQ ID NO. 36    AIKTSPKANKEIL

SEQ ID NO. 51    ELREA

T CELL RECEPTORS WHICH RECOGNIZE MUTATED EGFR

CROSS-REFERENCE TO RELATED APPLICATIONS

This patent application is a U.S. national stage of PCT/US2019/030108, filed May 1, 2019, which claims the benefit of U.S. Provisional Patent Application No. 62/665,234, filed May 1, 2018, each of which is incorporated by reference in its entirety herein.

STATEMENT REGARDING FEDERALLY SPONSORED RESEARCH AND DEVELOPMENT

This invention was made with Government support under project number Z01BC011651-03 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 85,226 Byte ASCII (Text) file named "750875_ST25.txt." dated Oct. 30, 2020.

BACKGROUND OF THE INVENTION

Some cancers may have very limited treatment options, particularly when the cancer becomes metastatic and unresectable. Despite advances in treatments such as, for example, surgery, chemotherapy, and radiation therapy, the prognosis for many cancers, such as, for example, non-small-cell lung cancer (NSCLC), may be poor. Accordingly, there exists an unmet need for additional treatments for cancer.

BRIEF SUMMARY OF THE INVENTION

An embodiment of the invention provides an isolated or purified T cell receptor (TCR) having antigenic specificity for the mutated epidermal growth factor receptor (EGFR) amino acid sequence of AIKTSPKANKEIL (SEQ ID NO: 36).

Further embodiments of the invention provide polypeptides, proteins, nucleic acids, recombinant expression vectors, host cells, populations of cells, and pharmaceutical compositions relating to the inventive TCRs.

Methods of detecting the presence of cancer in a mammal and methods of treating or preventing cancer in a mammal are further provided by embodiments of the invention.

DETAILED DESCRIPTION OF THE INVENTION

Figure 1:
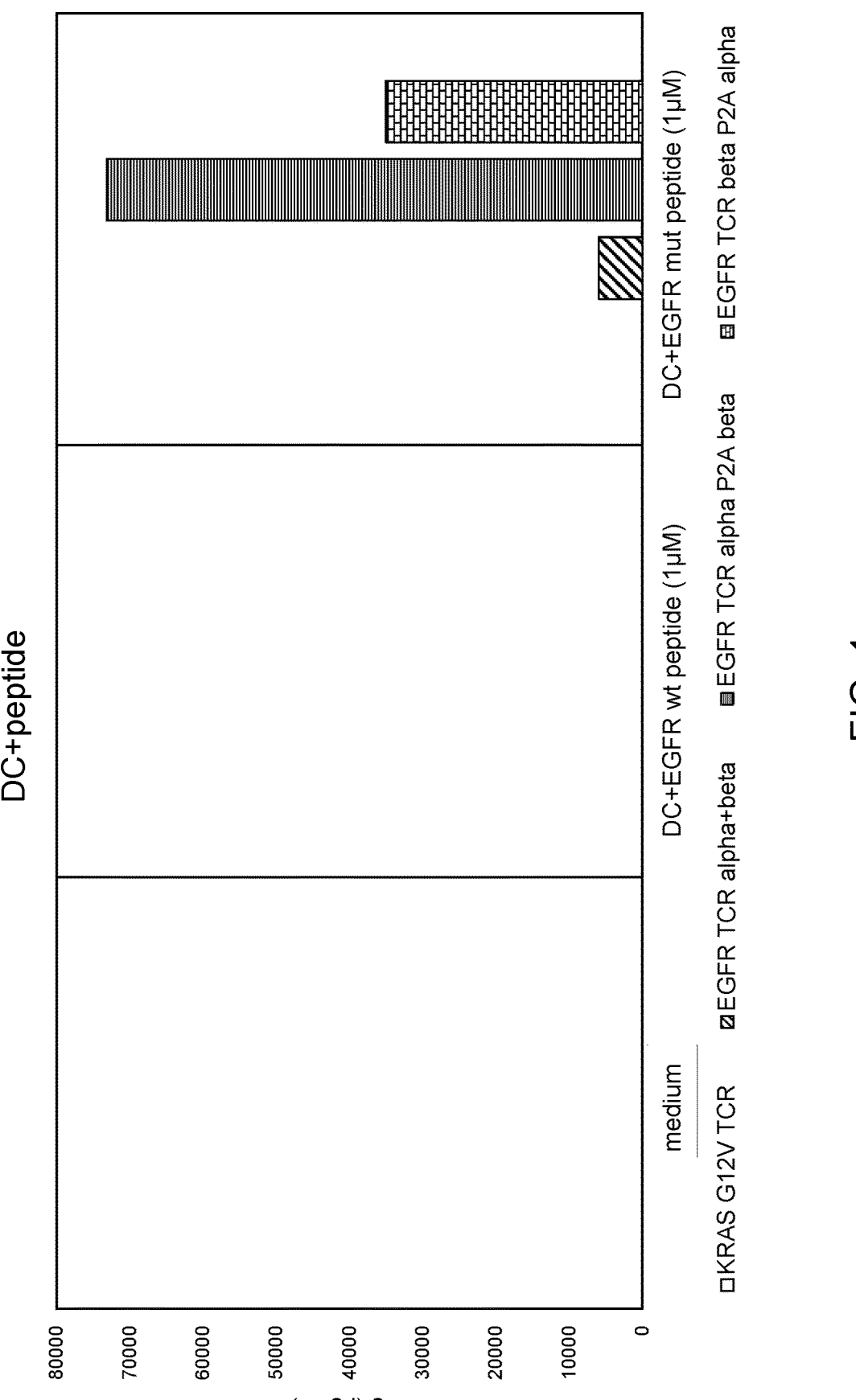
FIG. 1 is a graph showing the amount of IFN-γ (pg/ml) secreted upon co-culture of cells transduced with Construct 1 (EGFR TCR alpha P2A beta), Construct 2 (EGFR TCR beta P2A alpha), an anti-KRAS G12V TCR, or a mixture of vectors encoding the α and β chains (EGFR TCR alpha+ beta) with dendritic cells which had been pulsed with WT EGFR peptide or mutated EGFR (E746_A750 del) peptide. Transduced cells cultured alone (medium) served as a control.

EGFR (also referred to as ERBB1 or HER1) is a transmembrane glycoprotein that belongs to the receptor tyrosine kinase (RTK) super-family of cell surface receptors, which mediate cell signaling by extra-cellular growth factors. EGFR is a cell surface protein that binds to epidermal growth factor (EGF). Binding of EGFR to EGF induces receptor dimerization and tyrosine autophosphorylation and leads to cell proliferation. Examples of wild-type (WT), unmutated human EGFR amino acid sequences include those disclosed in GENBANK database Accession Nos. NP 001333826.1 (isoform e precursor), NP_001333827.1 (isoform f precursor), NP_001333828.1 (isoform g precursor), NP_001333829.1 (isoform h precursor), NP_001333870.1 (isoform i precursor), NP 005219.2 (isoform a precursor), NP_958439.1 (isoform b precursor), NP_958440.1 (isoform c precursor), and NP_958441.1 (isoform d precursor).

Mutations in EGFR may be associated with cancer. For example, EGFR mutations may be found in about 10% of NSCLC patients in the United States and in about 50% of NSCLC patients in Asia. The deletion of amino acid residues E746-A750 may account for about 30 to about 40% of EGFR mutations.

Amino acid residue position numbers of EGFR are defined herein by reference to the amino acid sequence of the full-length, WT, unmutated human EGFR amino acid sequence of SEQ ID NO: 1. The actual positions of the amino acid residues of a particular embodiment of an EGFR amino acid sequence are defined relative to the corresponding positions of SEQ ID NO: 1 and may represent different residue position numbers than the residue position numbers of SEQ ID NO: 1. An EGFR amino acid sequence (e.g., a EGFR peptide) may comprise fewer than all of the amino acid residues of the full-length, WT EGFR protein. For example, positions 746-750 are defined herein by reference to the WT full-length EGFR protein (namely, SEQ ID NO: 1) with the understanding that the actual position of the corresponding residue in a particular example of a EGFR amino acid sequence may be different. For example, when a particular example of a WT EGFR amino acid sequence is PEGEKVKIPVAIKELREATSPKANK (SEQ ID NO: 34) (an exemplary WT EGFR peptide corresponding to contiguous amino acid residues 733 to 757 of SEQ ID NO: 1), the deletion of EGFR amino acid residues 746-750 refer to a deletion of the underlined residues in SEQ ID NO: 34, even though the actual positions of the underlined residues in SEQ ID NO: 34 are 14-18, respectively.

The terms "EGFR E746_A750del" and "EGFR E746-A750 deletion" refer to a mutated EGFR amino acid sequence (i) in which all of the contiguous amino acid residues normally present at positions 746-750 of EGFR SEQ ID NO: 1 are absent and (ii) which comprises a suitable number of contiguous amino acid residues which flank each of the amino side and the carboxyl side of positions 746-750 of WT EGFR SEQ ID NO: 1. The number of contiguous amino acids from the WT EGFR protein flanking each side of the deleted amino acid residues 746-750 is not limited and may be, for example, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 or a range defined by any two of the foregoing values. In a preferred embodiment, the mutated EGFR amino acid sequence with the EGFR E746-A750 deletion is AIKTSPKANKEIL (SEQ ID NO: 36).

An embodiment of the invention provides an isolated or purified T cell receptor (TCR) having antigenic specificity for the mutated epidermal growth factor receptor (EGFR) amino acid sequence of AIKTSPKANKEIL (SEQ ID NO: 36).

In an embodiment of the invention, the mutated EGFR E746_A750del peptide has any length suitable for binding to any of the HLA Class II molecules described herein. For example, the TCR may have antigenic specificity for a mutated EGFR peptide with the E746-A750 deletion, the mutated EGFR peptide having a length of about 11 to about 30 amino acid residues, about 15 to about 25 amino acid residues, about 18 to about 22 amino acid residues, or about 8 to about 15 amino acid residues. In an embodiment of the invention, the TCR may have antigenic specificity for a EGFR peptide with the E746-A750 deletion, the mutated EGFR peptide having a length of about 8 amino acid residues, about 9 amino acid residues, about 10 amino acid residues, 11 amino acid residues, about 12 amino acid residues, about 13 amino acid residues, about 14 amino acid residues, about 15 amino acid residues, about 16 amino acid residues, about 17 amino acid residues, about 18 amino acid residues, about 19 amino acid residues, about 20 amino acid residues, about 21 amino acid residues, about 22 amino acid residues, about 23 amino acid residues, about 24 amino acid residues, about 25 amino acid residues, about 26 amino acid residues, about 27 amino acid residues, about 28 amino acid residues, about 29 amino acid residues, or about 30 amino acid residues. Examples of specific mutated EGFR peptides with the E746-A750 deletion, which may be recognized by the inventive TCR, include those set forth in Table A.

TABLE A

| SEQ ID NO: | Peptide |
| --- | --- |
| 35 | PEGEKVKIPVAIKTSPKANKEILDE |
| 36 | AIKTSPKANKEIL |
| 37 | AIKTSPKANKEI |
| 38 | IKTSPKANKEIL |
| 39 | IKTSPKANKEI |
| 40 | GEKVKIPVAIKTSPKANKEILDE |
| 41 | KVKIPVAIKTSPKANKEILDE |
| 42 | KIPVAIKTSPKANKEILDE |
| 43 | PVAIKTSPKANKEILDE |
| 44 | AIKTSPKANKEILDE |
| 46 | PEGEKVKIPVAIKTSPKANKEIL |

In an embodiment of the invention, the inventive TCRs are able to recognize EGFR E746_A750del presented by an HLA Class II molecule. In this regard, the TCR may elicit an immune response upon binding to EGFR E746_A750del within the context of an HLA Class II molecule. The inventive TCRs may bind to the HLA Class II molecule in addition to EGFR E746_A750del.

In an embodiment of the invention, the HLA Class II molecule is an HLA-DP molecule. The HLA-DP molecule is a heterodimer of an α chain (DPA) and β chain (DPB). The HLA-DPA chain may be any HLA-DPA chain. The HLA-DPB chain may be any HLA-DPB chain. In an embodiment of the invention, the HLA Class II molecule is a heterodimer of an HLA-DPA1 chain and an HLA-DPB1 chain. Examples of HLA-DPA1 molecules may include, but are not limited to, those encoded by the HLA-DPA1*01:03, HLA-DPA1*01:04, HLA-DPA1*01:05, HLA-DPA1*01:06, HLA-DPA1*01:07, HLA-DPA1*01:08, HLA-DPA1*01:09, HLA-DPA1*01:10, HLA-DPA1*02:01, HLA-DPA1*02:02, HLA-DPA1*02:03, HLA-DPA1*02:04, HLA-DPA1*03:01, HLA-DPA1*03:02, HLA-DPA1*03:03, and HLA-DPA1*04:01 alleles. Examples of HLA-DPB1 molecules may include, but are not limited to, those encoded by the HLA-DPB1*01:01, HLA-DPB1*02:01, HLA-DPB1*02:02, HLA-DPB1*03:01, HLA-DPB1*04:01, HLA-DPB1*04:02, HLA-DPB1*05:01, HLA-DPB1*06:01, HLA-DPB1*07:01, HLA-DPB1*08:01, HLA-DPB1*09:01, and HLA-DPB1*10:01 alleles. Preferably, the HLA Class II molecule is a heterodimer of an HLA-DPA1*02:01 chain and an HLA-DPB1*01:01 chain.

The TCRs of the invention may provide any one or more of a variety of advantages, including when expressed by cells used for adoptive cell transfer. EGFR with the E746-A750 deletion is expressed by cancer cells and is not expressed by normal, noncancerous cells. Without being bound to a particular theory or mechanism, it is believed that the inventive TCRs advantageously target the destruction of cancer cells while minimizing or eliminating the destruction of normal, non-cancerous cells, thereby reducing, for example, by minimizing or eliminating, toxicity. Moreover, the EGFR E746-A750 deletion is a "driver mutation," which drives the development of the cancer. Because the driver mutation is needed for the cancer cells to stay cancerous, substantially all of the cancer cells will have the driver mutation. A challenge in cancer treatment is the heterogeneity of cancer cells. Non-driver mutations, so called "passenger mutations," may exist in some cancer cells but not in all of the cancer cells. Even if a cancer treatment were to target and eliminate passenger mutation-positive cancer cells, the passenger mutation-negative cancer cells could still survive, which could limit the benefit for the patient. Without being bound to a particular theory or mechanism, it is believed that because the EGFR E746-A750 deletion is a driver mutation, the targeting of cells with this mutation will kill substantially all of the cancer cells.

Moreover, the inventive TCRs may, advantageously, successfully treat or prevent cancers which express EGFR with the E746-A750 deletion that do not respond to other types of treatment such as, for example, chemotherapy, surgery, or radiation. The inventive TCRs may provide highly avid recognition of EGFR with the E746-A750 deletion, which may provide the ability to recognize unmanipulated tumor cells (e.g., tumor cells that have not been treated with interferon (IFN)-γ; transfected with a vector encoding one or more of EGFR E746_A750del peptide, HLA-DPA1*02:01 chain, and HLA-DPB1*01:01 chain; pulsed with a EGFR E746_A750del peptide; or a combination thereof). Moreover, the HLA-DPA1*02:01 chain and HLA-DPB1*01:01 chain alleles are expressed by about 10% of Caucasians and about 50% of African Americans in the U.S. Accordingly, the inventive TCRs may increase the number of immunotherapy-eligible cancer patients to include those patients that express the HLA-DPA1*02:01 and HLA-DPB1*01:01 alleles who may not be eligible for immunotherapy using TCRs that recognize EGFR E746_A750del presented by other MHC molecules.

The phrase "antigenic specificity," as used herein, means that the TCR can specifically bind to and immunologically recognize mutated EGFR with the E746-A750 deletion with high avidity. For example, a TCR may be considered to have "antigenic specificity" for EGFR E746_A750del if about $1 \times 10^4$ to about $1 \times 10^5$ T cells expressing the TCR secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, 20,000 pg/mL or more, or a range defined by any two of the foregoing values) of IFN-γ upon co-culture with (a) antigen-negative, HLA Class II molecule positive target cells pulsed with a low concentration of EGFR E746_A750del peptide (e.g., about 0.05 ng/mL to about 10 ng/mL, 1 ng/mL, 2 ng/mL, 5 ng/mL, 8 ng/mL, 10 ng/mL, or a range defined by any two of the foregoing values) or (b) antigen-negative, HLA Class II molecule positive target cells into which a nucleotide sequence encoding EGFR E746_A750del has been introduced such that the target cell expresses EGFR E746_A750del. Cells expressing the inventive TCRs may also secrete IFN-γ upon co-culture with antigen-negative, HLA Class II molecule positive target cells pulsed with higher concentrations of EGFR E746_A750del. The HLA Class II molecule may be a heterodimer of an HLA-DPA1*02:01 chain and an HLA-DPB1*01:01 chain.

Alternatively or additionally, a TCR may be considered to have "antigenic specificity" for EGFR E746_A750del if T cells expressing the TCR secrete at least twice as much IFN-γ upon co-culture with (a) antigen-negative, HLA Class II molecule positive target cells pulsed with a low concentration of EGFR E746_A750del peptide or (b) antigen-negative, HLA Class II molecule positive target cells into which a nucleotide sequence encoding EGFR E746_A750del has been introduced such that the target cell expresses EGFR E746_A750del as compared to the amount of IFN-γ expressed by a negative control. The negative control may be, for example, (i) T cells expressing the TCR, co-cultured with (a) antigen-negative, HLA Class II molecule positive target cells pulsed with the same concentration of an irrelevant peptide (e.g., some other peptide with a different sequence from the EGFR E746_A750del peptide) or (b) antigen-negative, HLA Class II molecule positive target cells into which a nucleotide sequence encoding an irrelevant peptide has been introduced such that the target cell expresses the irrelevant peptide, or (ii) untransduced T cells (e.g., derived from PBMC, which do not express the TCR) co-cultured with (a) antigen-negative, HLA Class II molecule positive target cells pulsed with the same concentration of EGFR E746_A750del peptide or (b) antigen-negative, HLA Class II molecule positive target cells into which a nucleotide sequence encoding EGFR E746_A750del has been introduced such that the target cell expresses EGFR E746_A750del. The HLA Class II molecule expressed by the target cells of the negative control would be the same HLA Class II molecule expressed by the target cells that are co-cultured with the T cells being tested. The HLA Class II molecule may be a heterodimer of an HLA-DPA1*02:01 chain and an HLA-DPB1*01:01 chain. IFN-γ secretion may be measured by methods known in the art such as, for example, enzyme-linked immunosorbent assay (ELISA).

Alternatively or additionally, a TCR may be considered to have "antigenic specificity" for mutated EGFR with the E746-A750 deletion if at least twice as many of the numbers of T cells expressing the TCR secrete IFN-γ upon co-culture with (a) antigen-negative, HLA Class II molecule positive target cells pulsed with a low concentration of EGFR E746_A750del peptide or (b) antigen-negative, HLA Class II molecule positive target cells into which a nucleotide sequence encoding EGFR E746_A750del has been introduced such that the target cell expresses EGFR E746_A750del as compared to the numbers of negative control T cells that secrete IFN-γ. The HLA Class II molecule, concentration of peptide, and the negative control may be as described herein with respect to other aspects of the invention. The numbers of cells secreting IFN-γ may be measured by methods known in the art such as, for example, ELISPOT.

Alternatively or additionally, a TCR may be considered to have "antigenic specificity" for EGFR E746_A750del if T cells expressing the TCR upregulate expression of one or more T-cell activation markers as measured by, for example, flow cytometry after stimulation with target cells expressing mutated EGFR. Examples of T-cell activation markers include 4-1BB, OX40, CD107a, CD69, and cytokines that are upregulated upon antigen stimulation (e.g., tumor necrosis factor (TNF), interleukin (IL)-2, etc.).

An embodiment of the invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for EGFR E746_A750del.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 3 (CDR1 of α chain), a CDR2 comprising the amino acid sequence of SEQ ID NO: 4 (CDR2 of α chain), and a CDR3 comprising the amino acid sequence of SEQ ID NO: 5 (CDR3 of α chain), and a second polypeptide chain comprising a CDR1 comprising the amino acid sequence of SEQ ID NO: 6 (CDR1 of β chain), a CDR2 comprising the amino acid sequence of SEQ ID NO: 7 (CDR2 of β chain), and a CDR3 comprising the amino acid sequence of SEQ ID NO: 8 (CDR3 of β chain). In this regard, the inventive TCR can comprise any one or more of the amino acid sequences selected from the group consisting of SEQ ID NOs: 3-8. In an embodiment of the invention, the TCR comprises the amino acid sequences of: (a) all of SEQ ID NOs: 3-5, (b) all of SEQ ID NOs: 6-8, or (c) all of SEQ ID NOs: 3-8. In an especially preferred embodiment, the TCR comprises the amino acid sequences of all of SEQ ID NOs: 3-8.

In an embodiment of the invention, the TCR comprises an amino acid sequence of a variable region of a TCR comprising the CDRs set forth above. The TCR may comprise a human variable region, e.g., a human α chain variable region and a human β chain variable region. In this regard, the TCR can comprise the amino acid sequence of: SEQ ID NO: 9 (variable region of α chain); SEQ ID NO: 10 (variable region of β chain); SEQ ID NO: 11 (variable region of α chain); SEQ ID NO: 12 (variable region of β chain); both of SEQ ID NOs: 9 and 10, or both of SEQ ID NO: 11 and 12. Preferably, the TCR comprises the amino acid sequences of both of SEQ ID NOs: 9 and 10 or both of SEQ ID NO: 11 and 12.

The inventive TCRs may further comprise an α chain constant region and a β chain constant region. The constant region may be derived from any suitable species such as, e.g., human or mouse. In an embodiment of the invention, the TCRs further comprise murine α and β chain constant regions or human α and β chain constant regions. As used herein, the term "murine" or "human," when referring to a TCR or any component of a TCR described herein (e.g., complementarity determining region (CDR), variable region, constant region, α chain, and/or β chain), means a TCR (or component thereof) which is derived from a mouse or a human, respectively, i.e., a TCR (or component thereof) that originated from or was, at one time, expressed by a mouse T cell or a human T cell, respectively.

In an embodiment of the invention, the TCR comprises a human constant region. The TCR may comprise the amino acid sequence of SEQ ID NO: 13 (wild-type (WT) human α chain constant region), SEQ ID NO: 14 (WT human β chain constant region), or both SEQ ID NOs: 13 and 14. Preferably, the inventive TCR comprises the amino acid sequences of both of SEQ ID NOs: 13 and 14. The TCR may comprise any of the human constant regions described herein in combination with any of the CDR regions as described herein with respect to other aspects of the invention. In this regard, the TCR may comprise the amino acid sequences of: (a) all of SEQ ID NOs: 3-5 and 13; (b) all of SEQ ID NOs: 6-8 and 14; or (c) all of SEQ ID NOs: 3-8 and 13-14. In another embodiment of the invention, the TCR may comprise any of the human constant regions described herein in combination with any of the variable regions described herein with respect to other aspects of the invention. In this regard, the TCR may comprise the amino acid sequences of: (i) both of SEQ ID NOs: 9 and 13; (ii) both of SEQ ID NOs: 10 and 14; (iii) all of SEQ ID NOs: 9-10 and 13-14; (iv) both of SEQ ID NOs: 11 and 13; (v) both of SEQ ID NOs: 12 and 14; or (vi) all of SEQ ID NOs: 11-12 and 13-14.

In another embodiment of the invention, the TCR comprises the amino acid sequence(s) of: SEQ ID NO: 19 (α chain with human constant region), SEQ ID NO: 20 (β chain with human constant region), or both of SEQ ID NO: 19-20.

An embodiment of the invention provides a chimeric TCR comprising a human variable region and a murine constant region, wherein the TCR has antigenic specificity for the mutated epidermal growth factor receptor (EGFR) amino acid sequence of AIKTSPKANKEIL (SEQ ID NO: 36). The murine constant region may provide any one or more advantages. For example, the murine constant region may diminish mispairing of the inventive TCR with the endogenous TCRs of the host cell into which the inventive TCR is introduced. Alternatively or additionally, the murine constant region may increase expression of the inventive TCR as compared to the same TCR with a human constant region. The chimeric TCR may comprise the amino acid sequence of SEQ ID NO: 17 (wild-type (WT) murine α chain constant region), SEQ ID NO: 18 (WT murine β chain constant region), or both SEQ ID NOs: 17 and 18. Preferably, the inventive TCR comprises the amino acid sequences of both of SEQ ID NOs: 17 and 18. The chimeric TCR may comprise any of the murine constant regions described herein in combination with any of the CDR regions as described herein with respect to other aspects of the invention. In this regard, the TCR may comprise the amino acid sequences of: (a) all of SEQ ID NOs: 3-5 and 17; (b) all of SEQ ID NOs: 6-8 and 18; or (c) all of SEQ ID NOs: 3-8 and 17-18. In another embodiment of the invention, the chimeric TCR may comprise any of the murine constant regions described herein in combination with any of the variable regions described herein with respect to other aspects of the invention. In this regard, the TCR may comprise the amino acid sequences of: (i) both of SEQ ID NOs: 9 and 17; (ii) both of SEQ ID NOs: 10 and 18; (iii) all of SEQ ID NOs: 9-10 and 17-18; (iv) both of SEQ ID NOs: 11 and 17; (v) both of SEQ ID NOs: 12 and 18; or (vi) all of SEQ ID NOs: 11-12 and 17-18.

In an embodiment of the invention, the TCR comprises a substituted constant region. In this regard, the TCR may comprise the amino acid sequence of any of the TCRs described herein with one, two, three, or four amino acid substitution(s) in the constant region of one or both of the α and β chain. Preferably, the TCR comprises a murine constant region with one, two, three, or four amino acid substitution(s) in the murine constant region of one or both of the α and β chains. In an especially preferred embodiment, the TCR comprises a murine constant region with one, two, three, or four amino acid substitution(s) in the murine constant region of the α chain and one amino acid substitution in the murine constant region of the β chain. In some embodiments, the TCRs comprising the substituted constant region advantageously provide one or more of increased recognition of targets which express mutated EGFR with the E746-A750 deletion, increased expression by a host cell, diminished mispairing with endogenous TCRs, and increased anti-tumor activity as compared to the parent TCR comprising an unsubstituted (wild-type) constant region. In general, the substituted amino acid sequences of the murine constant regions of the TCR α and β chains, SEQ ID NOs: 15 and 16, respectively, correspond with all or portions of the unsubstituted murine constant region amino acid sequences SEQ ID NOs: 17 and 18, respectively, with SEQ ID NO: 15 having one, two, three, or four amino acid substitution(s) when compared to SEQ ID NO: 17 and SEQ ID NO: 16 having one amino acid substitution when compared to SEQ ID NO: 18. In this regard, an embodiment of the invention provides a TCR comprising the amino acid sequences of (a) SEQ ID NO: 15 (constant region of α chain), wherein (i) X at position 48 is Thr or Cys; (ii) X at position 112 is Ser, Ala, Val, Leu, Ile, Pro, Phe, Met, or Trp; (iii) X at position 114 is Met, Ala, Val, Leu, Ile, Pro, Phe, or Trp; and (iv) X at position 115 is Gly, Ala, Val, Leu, Ile, Pro, Phe, Met, or Trp; (b) SEQ ID NO: 16 (constant region of f3 chain), wherein X at position 57 is Ser or Cys; or (c) both of SEQ ID NOs: 15 and 16. In an embodiment of the invention, the TCR comprising SEQ ID NO: 15 does not comprise SEQ ID NO: 17 (unsubstituted murine constant region of α chain). In an embodiment of the invention, the TCR comprising SEQ ID NO: 16 does not comprise SEQ ID NO: 18 (unsubstituted murine constant region of β chain).

In an embodiment of the invention, the TCR comprises an α chain comprising a variable region and a constant region and a β chain comprising a variable region and a constant region. In this regard, the TCR may comprise (a) an α chain comprising the amino acid sequence of SEQ ID NO: 21, wherein: (i) X at position 181 of SEQ ID NO: 21 is Thr or Cys; (ii) X at position 245 of SEQ ID NO: 21 is Ser, Ala, Val, Leu, Ile, Pro, Phe, Met, or Trp; (iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp; (b) a β chain comprising the amino acid sequence of SEQ ID NO: 22, wherein X at position 188 of SEQ ID NO: 22 is Ser or Cys; or (c) both (a) and (b). In an embodiment of the invention, the TCR comprising SEQ ID NO: 21 does not comprise SEQ ID NO: 17 (unsubstituted murine constant region of α chain). In an embodiment of the invention, the TCR comprising SEQ ID NO: 22 does not comprise SEQ ID NO: 18 (unsubstituted murine constant region of β chain).

In an embodiment of the invention, the substituted constant region includes cysteine substitutions in the constant region of one or both of the α and β chains to provide a cysteine-substituted TCR. Opposing cysteines in the α and the β chains provide a disulfide bond that links the constant regions of the α and the β chains of the substituted TCR to one another and which is not present in a TCR comprising the unsubstituted murine constant regions. In this regard, the TCR may be a cysteine-substituted TCR in which one or both of the native Thr at position 48 (Thr48) of SEQ ID NO: 17 and the native Ser at position 57 (Ser57) of SEQ ID NO: 18 may be substituted with Cys. Preferably, both of the native Thr48 of SEQ ID NO: 17 and the native Ser57 of SEQ ID NO: 18 are substituted with Cys. Examples of cysteine-substituted TCR constant regions sequences are set forth in Table 1. In an embodiment of the invention, the cysteine-substituted TCR comprises (i) SEQ ID NO: 15, (ii) SEQ ID NO: 16, or (iii) both of SEQ ID NOs: 15 and 16, wherein both of SEQ ID NOs: 15 and 16 are as defined in Table 1. The cysteine-substituted TCRs of the invention may include the substituted constant region in addition to any of the CDRs or variable regions described herein.

In an embodiment of the invention, the cysteine-substituted, chimeric TCR comprises a full length alpha chain and a full-length beta chain. Examples of cysteine-substituted, chimeric TCR alpha chain and beta chain sequences are set forth in Table 1. In an embodiment of the invention, the TCR comprises (i) SEQ ID NO: 21, (ii) SEQ ID NO: 22, or (iii) both of SEQ ID NO: 21 and 22, wherein SEQ ID NOs: 21-22 are as defined in Table 1.

TABLE 1

| SEQ ID NO: | Definitions of "X" |
|---|---|
| SEQ ID NO: 15 (constant region α chain) | X at position 48 is Cys, X at position 112 is Ser, X at position 114 is Met, and X at position 115 is Gly. |
| SEQ ID NO: 16 (constant region β chain) | X at position 57 is Cys |
| SEQ ID NO: 21 (α chain) | X at position 181 is Cys, X at position 245 is Ser, X at position 247 is Met, and X at position 248 is Gly. |
| SEQ ID NO: 22 (β chain) | X at position 188 is Cys |

In an embodiment of the invention, the substituted amino acid sequence includes substitutions of one, two, or three amino acids in the transmembrane (TM) domain of the constant region of one or both of the α and β chains with a hydrophobic amino acid to provide a hydrophobic amino acid-substituted TCR (also referred to herein as an "LVL-modified TCR"). The hydrophobic amino acid substitution (s) in the TM domain of the TCR may increase the hydrophobicity of the TM domain of the TCR as compared to a TCR that lacks the hydrophobic amino acid substitution(s) in the TM domain. In this regard, the TCR is an LVL-modified TCR in which one, two, or three of the native Ser112, Met114, and Gly115 of SEQ ID NO: 17 may, independently, be substituted with Ala, Val, Leu, Ile, Pro, Phe, Met, or Trp; preferably with Leu, Ile, or Val. Preferably, all three of the native Ser112, Met114, and Gly115 of SEQ ID NO: 17 may, independently, be substituted with Ala, Val, Leu, Ile, Pro, Phe, Met, or Trp; preferably with Leu, Ile, or Val. In an embodiment of the invention, the LVL-modified TCR comprises (i) SEQ ID NO: 15, (ii) SEQ ID NO: 16, or (iii) both of SEQ ID NOs: 15 and 16, wherein both of SEQ ID NOs: 15 and 16 are as defined in Table 2. The LVL-modified TCRs of the invention may include the substituted constant region in addition to any of the CDRs or variable regions described herein.

In an embodiment of the invention, the LVL-modified TCR comprises a full length alpha chain and a full-length beta chain. Examples of LVL-modified TCR alpha chain and beta chain sequences are set forth in Table 2. In an embodiment of the invention, the LVL-modified TCR comprises (i) SEQ ID NO: 21, (ii) SEQ ID NO: 22, or (iii) both of SEQ ID NO: 21 and 22, wherein SEQ ID NOs: 21-22 are as defined in Table 2.

TABLE 2

| SEQ ID NO: | Definitions of "X" |
|---|---|
| SEQ ID NO: 15 (constant region α chain) | X at position 48 is Thr; X at position 112 is Ser, Ala, Val, Leu, Ile, Pro, Phe, Met, or Trp; preferably wherein X at position 112 is Leu, Ile, or Val; especially preferably wherein X at position 112 is Leu; X at position 114 is Met, Ala, Val, Leu, Ile, Pro, Phe, or Trp; preferably wherein X at position 114 is Leu, Ile, or Val; especially preferably wherein X at position 114 is Ile; and X at position 115 is Gly, Ala, Val, Leu, Ile, Pro, Phe, Met, or Trp; preferably wherein X at position 115 is Leu, Ile, or Val; especially preferably wherein X at position 115 is Val; Wherein SEQ ID NO: 15 does not comprise SEQ ID NO: 17 (unsubstituted constant region of alpha chain) |

TABLE 2-continued

| SEQ ID NO: | Definitions of "X" |
| --- | --- |
| SEQ ID NO: 16 (constant region β chain) | X at position 57 is Ser |
| SEQ ID NO: 21 (α chain) | X at position 181 is Thr; X at position 245 is Ser, Ala, Val, Leu, Ile, Pro, Phe, Met, or Trp; preferably wherein X at position 245 is Leu, Ile, or Val; especially preferably wherein X at position 245 is Leu; X at position 247 is Met, Ala, Val, Leu, Ile, Pro, Phe, or Trp; preferably wherein X at position 247 is Leu, Ile, or Val; especially preferably wherein X at position 247 is Ile; and X at position 248 is Gly, Ala, Val, Leu, Ile, Pro, Phe, Met, or Trp; preferably wherein X at position 248 is Leu, Ile, or Val; especially preferably wherein X at position 248 is Val, Wherein SEQ ID NO: 21 does not comprise SEQ ID NO: 17 (unsubstituted murine alpha chain constant region) |
| SEQ ID NO: 22 (β chain) | X at position 188 is Ser |

In an embodiment of the invention, the substituted amino acid sequence includes the cysteine substitutions in the constant region of one or both of the α and β chains in combination with the substitution(s) of one, two, or three amino acids in the transmembrane (TM) domain of the constant region of one or both of the α and β chains with a hydrophobic amino acid (also referred to herein as "cysteine-substituted, LVL-modified TCR"). In this regard, the TCR is a cysteine-substituted, LVL-modified, chimeric TCR in which the native Thr48 of SEQ ID NO: 17 is substituted with Cys; one, two, or three of the native Ser112, Met114, and Gly115 of SEQ ID NO: 17 are, independently, substituted with Ala, Val, Leu, Ile, Pro, Phe, Met, or Trp; preferably with Leu, Ile, or Val; and the native Ser57 of SEQ ID NO: 18 is substituted with Cys. Preferably, all three of the native Ser112, Met114, and Gly115 of SEQ ID NO: 17 may, independently, be substituted with Ala, Val, Leu, Ile, Pro, Phe, Met, or Trp; preferably with Leu, Ile, or Val. In an embodiment of the invention, the cysteine-substituted, LVL-modified TCR comprises (i) SEQ ID NO: 15, (ii) SEQ ID NO: 16, or (iii) both of SEQ ID NOs: 15 and 16, wherein both of SEQ ID NOs: 15 and 16 are as defined in Table 3. The cysteine-substituted, LVL-modified TCRs of the invention may include the substituted constant region in addition to any of the CDRs or variable regions described herein.

In an embodiment, the cysteine-substituted, LVL-modified TCR comprises a full-length alpha chain and a full-length beta chain. In an embodiment of the invention, the cysteine-substituted, LVL-modified TCR comprises (i) SEQ ID NO: 21, (ii) SEQ ID NO: 22, or (iii) both of SEQ ID NO: 21 and 22, wherein SEQ ID NOs: 21-22 are as defined in Table 3. In a preferred embodiment, the cysteine-substituted, LVL-modified TCR comprises (i) SEQ ID NO: 23 (a full-length alpha chain), (ii) SEQ ID NO: 24 (full-length beta chain), or (iii) both of SEQ ID NOs 23-24. Preferably, the cysteine-substituted, LVL-modified TCR comprises both of SEQ ID NOs: 23-24.

TABLE 3

| SEQ ID NO: | Definitions of "X" |
| --- | --- |
| SEQ ID NO: 15 (constant region α chain) | X at position 48 is Cys; X at position 112 is Ser, Ala, Val, Leu, Ile, Pro, Phe, Met, or Trp; preferably wherein X at position 112 is Leu, Ile, or Val; especially preferably wherein X at position 112 |

TABLE 3-continued

| SEQ ID NO: | Definitions of "X" |
| --- | --- |
| | is Leu; X at position 114 is Met, Ala, Val, Leu, Ile, Pro, Phe, or Trp; preferably wherein X at position 114 is Leu, Ile, or Val; especially preferably wherein X at position 114 is Ile; and X at position 115 is Gly, Ala, Val, Leu, Ile, Pro, Phe, Met, or Trp; preferably wherein X at position 115 is Leu, Ile, or Val; and especially preferably wherein X at position 115 is Val, wherein SEQ ID NO: 15 does not simultaneously comprise all of Ser at position 112, Met at position 114, and Gly at position 115. |
| SEQ ID NO: 16 (constant region β chain) | X at position 57 is Cys |
| SEQ ID NO: 21 (α chain) | X at position 181 is Cys; X at position 245 is Ser, Ala, Val, Leu, Ile, Pro, Phe, Met, or Trp; preferably wherein X at position 245 is Leu, Ile, or Val; especially preferably wherein X at position 245 is Leu; X at position 247 is Met, Ala, Val, Leu, Ile, Pro, Phe, or Trp; preferably wherein X at position 247 is Leu, Ile, or Val; especially preferably wherein X at position 247 is Ile; and X at position 248 is Gly, Ala, Val, Leu, Ile, Pro, Phe, Met, or Trp; preferably wherein X at position 248 is Leu, Ile, or Val; and especially preferably wherein X at position 248 is Val, wherein SEQ ID NO: 21 does not simultaneously comprise all of Ser at position 245, Met at position 247, and Gly at position 248. |
| SEQ ID NO: 22 (β chain) | X at position 188 is Cys |

Also provided by an embodiment of the invention is a polypeptide comprising a functional portion of any of the TCRs described herein. The term "polypeptide," as used herein, includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to EGFR E746_A750del. The term "functional portion," when used in reference to a TCR, refers to any part or fragment of the TCR of the invention, which part or fragment retains the biological activity of the TCR of which it is a part (the parent TCR). Functional portions encompass, for example, those parts of a TCR that retain the ability to specifically bind to EGFR E746_A750del (e.g., within the context of a HLA Class II molecule), or detect, treat, or prevent cancer, to a similar extent, the same extent, or to a higher extent, as the parent TCR. In reference to the parent TCR, the functional portion can comprise, for instance, about 10%, about 25%, about 30%, about 50%, about 70%, about 80%, about 90%, about 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to EGFR E746_A750del; and/or having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one or more of the CDR1, CDR2, and CDR3 of the variable region(s) of the α chain and/or β chain of a TCR of the invention. In an embodiment of the invention, the polypeptide can comprise the amino acid sequence of SEQ ID NO: 3 (CDR1 of α chain), SEQ ID NO: 4 (CDR2 of α chain), SEQ ID NO: 5 (CDR3 of α chain), SEQ ID NO: 6 (CDR1 of β chain), SEQ ID NO: 7 (CDR2 of β chain), SEQ ID NO: 8 (CDR3 of β chain), or a combination thereof.

In this regard, the inventive polypeptide can comprise any one or more of the amino acid sequences selected from the group consisting of SEQ ID NOs: 3-8. In an embodiment of the invention, the TCR comprises the amino acid sequences of: (a) all of SEQ ID NOs: 3-5, (b) all of SEQ ID NOs: 6-8, or (c) all of SEQ ID NOs: 3-8. In a preferred embodiment, the polypeptide comprises the amino acid sequences of all of SEQ ID NOs: 3-8.

In an embodiment of the invention, the inventive polypeptide can comprise, for instance, the variable region of the inventive TCR comprising a combination of the CDR regions set forth above. In this regard, the polypeptide can comprise the amino acid sequence of (i) SEQ ID NO: 9 (variable region of α chain), (ii) SEQ ID NO: 10 (variable region of β chain), (iii) both of SEQ ID NOs: 9 and 10, (iv) SEQ ID NO: 11 (variable region of α chain), (v) SEQ ID NO: 12 (variable region of β chain), or (vi) both of SEQ ID NOs: 11 and 12. Preferably, the polypeptide comprises the amino acid sequences of both of SEQ ID NOs: 9 and 10 or both of SEQ ID NOs: 11 and 12.

In an embodiment of the invention, the inventive polypeptide can further comprise the constant region of the inventive TCR set forth above. In this regard, the polypeptide can further comprise the amino acid sequence of SEQ ID NO: 17 (WT murine constant region of α chain), SEQ ID NO: 18 (WT murine constant region of β chain), SEQ ID NO: 15, (substituted murine constant region of α chain), SEQ ID NO: 16 (substituted murine constant region of β chain), both SEQ ID NOs: 15 and 16, or both SEQ ID NOs: 17 and 18. Preferably, the polypeptide further comprises the amino acid sequences of both of SEQ ID NOs: 15 and 16 or both of SEQ ID NO: 17 and 18 in combination with any of the CDR regions or variable regions described herein with respect to other aspects of the invention.

In an embodiment of the invention, the polypeptide comprises: (a) the amino acid sequence of SEQ ID NO: 15, wherein: (i) X at position 48 of SEQ ID NO: 15 is Thr or Cys; (ii) X at position 112 of SEQ ID NO: 15 is Ser, Ala, Val, Leu, Ile, Pro, Phe, Met, or Trp; (iii) X at position 114 of SEQ ID NO: 15 is Met, Ala, Val, Leu, Ile, Pro, Phe, or Trp; and (iv) X at position 115 of SEQ ID NO: 15 is Gly, Ala, Val, Leu, Ile, Pro, Phe, Met, or Trp; (b) the amino acid sequence of SEQ ID NO: 16, wherein X at position 57 of SEQ ID NO: 16 is Ser or Cys; or (c) both (a) and (b). In an embodiment of the invention, one or both of SEQ ID NOs: 15 and 16 of the polypeptide are as defined in any one of Tables 1-3.

In an embodiment of the invention, the inventive polypeptide can comprise the entire length of an α or β chain of the TCR described herein. In this regard, the inventive polypeptide can comprise the amino acid sequence of SEQ ID NO: 21, SEQ ID NO: 22, SEQ ID NO: 23, SEQ ID NO: 24, both of SEQ ID NOs: 21 and 22, or both of SEQ ID NOs: 23 and 24. Preferably, the polypeptide comprises the amino acid sequences of both of SEQ ID NOs: 21 and 22 or both of SEQ ID NOs: 23 and 24.

In an embodiment of the invention, the polypeptide comprises: (a) the amino acid sequence of SEQ ID NO: 21, wherein: (i) X at position 181 of SEQ ID NO: 21 is Thr or Cys; (ii) X at position 245 of SEQ ID NO: 21 is Ser, Ala, Val, Leu, Ile, Pro, Phe, Met, or Trp; (iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp; (b) the amino acid sequence of SEQ ID NO: 22, wherein X at position 188 of SEQ ID NO: 22 is Ser or Cys; or (c) both (a) and (b). In an embodiment of the invention, any one or more of SEQ ID NOs: 21-22 of the polypeptide are as defined in any one of Tables 1-3.

An embodiment of the invention further provides a protein comprising at least one of the polypeptides described herein. By "protein" is meant a molecule comprising one or more polypeptide chains.

In an embodiment, the protein of the invention can comprise a first polypeptide chain comprising the amino acid sequences of SEQ ID NOs: 3-5 and a second polypeptide chain comprising the amino acid sequence of SEQ ID NOs: 6-8.

In another embodiment of the invention, the protein may comprise (a) a first polypeptide chain comprising the amino acid sequences of SEQ ID NO: 9 and a second polypeptide chain comprising the amino acid sequences of SEQ ID NO: 10; or (b) a first polypeptide chain comprising the amino acid sequences of SEQ ID NO: 11 and a second polypeptide chain comprising the amino acid sequences of SEQ ID NO: 12.

The inventive protein may further comprise any of the constant regions described herein with respect to other aspects of the invention. In this regard, in an embodiment of the invention, the first polypeptide chain may further comprise the amino acid sequence of SEQ ID NO: 17 and the second polypeptide chain may further comprise the amino acid sequence of SEQ ID NO: 18. In an embodiment of the invention, the first polypeptide chain may further comprise the amino acid sequence of SEQ ID NO: 15 and the second polypeptide chain may further comprise the amino acid sequence of SEQ ID NO: 16.

In an embodiment of the invention, the protein comprises: (a) a first polypeptide chain comprising the amino acid sequence of SEQ ID NO: 15, wherein: (i) X at position 48 of SEQ ID NO: 15 is Thr or Cys; (ii) X at position 112 of SEQ ID NO: 15 is Ser, Ala, Val, Leu, Ile, Pro, Phe, Met, or Trp; (iii) X at position 114 of SEQ ID NO: 15 is Met, Ala, Val, Leu, Ile, Pro, Phe, or Trp; and (iv) X at position 115 of SEQ ID NO: 15 is Gly, Ala, Val, Leu, Ile, Pro, Phe, Met, or Trp; (b) a second polypeptide chain comprising the amino acid sequence of SEQ ID NO: 16, wherein X at position 57 of SEQ ID NO: 16 is Ser or Cys; or (c) both (a) and (b). In an embodiment of the invention, one or both of SEQ ID NOs: 15 and 16 of the protein are as defined in any one of Tables 1-3.

Alternatively or additionally, the protein of an embodiment of the invention can comprise (a) a first polypeptide chain comprising the amino acid sequence of SEQ ID NO: 21, wherein: (i) X at position 181 of SEQ ID NO: 21 is Thr or Cys; (ii) X at position 245 of SEQ ID NO: 21 is Ser, Ala, Val, Leu, Ile, Pro, Phe, Met, or Trp; (iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp; (b) a second polypeptide chain comprising the amino acid sequence of SEQ ID NO: 22, wherein X at position 188 of SEQ ID NO: 22 is Ser or Cys; or (c) both (a) and (b). In an embodiment of the invention, one or both of SEQ ID NOs: 21-22 are as defined in any one of Tables 1-3. In an embodiment of the invention, the protein may comprise a first polypeptide chain comprising the amino acid sequence of SEQ ID NO: 23 and a second polypeptide chain comprising the amino acid sequence of SEQ ID NO: 24.

The protein of the invention can be a TCR. Alternatively, if, for example, the protein comprises a single polypeptide chain comprising the amino acid sequences of both SEQ ID NOs: 21 and 22, both SEQ ID NOs: 23 and 24, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, an embodiment of the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs, polypeptides, and proteins of the invention may be expressed as a single protein comprising a linker peptide linking the α chain and the β chain. In this regard, the TCRs, polypeptides, and proteins of the invention may further comprise a linker peptide. The linker peptide may advantageously facilitate the expression of a recombinant TCR, polypeptide, and/or protein in a host cell. The linker peptide may comprise any suitable amino acid sequence. For example, the linker peptide may be a P2A linker comprising the amino acid sequence of SEQ ID NO:25. Upon expression of the construct including the linker peptide by a host cell, the linker peptide may be cleaved, resulting in separated α and β chains. In an embodiment of the invention, the TCR, polypeptide, or protein may comprise an amino acid sequence comprising a full-length α chain, a full-length β chain, and a linker peptide positioned between the α and β chains.

The protein of the invention can be a recombinant antibody, or an antigen binding portion thereof, comprising at least one of the inventive polypeptides described herein. As used herein, "recombinant antibody" refers to a recombinant (e.g., genetically engineered) protein comprising at least one of the polypeptides of the invention and a polypeptide chain of an antibody, or an antigen binding portion thereof. The polypeptide of an antibody, or antigen binding portion thereof, can be a heavy chain, a light chain, a variable or constant region of a heavy or light chain, a single chain variable fragment (scFv), or an Fc, Fab, or F(ab)₂' fragment of an antibody, etc. The polypeptide chain of an antibody, or an antigen binding portion thereof, can exist as a separate polypeptide of the recombinant antibody. Alternatively, the polypeptide chain of an antibody, or an antigen binding portion thereof, can exist as a polypeptide, which is expressed in frame (in tandem) with the polypeptide of the invention. The polypeptide of an antibody, or an antigen binding portion thereof, can be a polypeptide of any antibody or any antibody fragment, including any of the antibodies and antibody fragments described herein.

Included in the scope of the invention are functional variants of the inventive TCRs, polypeptides, or proteins described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to EGFR E746_A750del for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, about 50%, about 75%, about 80%, about 90%, about 95%, about 96%, about 97%, about 98%, about 99% or more identical in amino acid sequence to the parent TCR, polypeptide, or protein, respectively.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the TCR, polypeptide, or protein, e.g., other amino acids, do not materially change the biological activity of the TCR, polypeptide, or protein. In this regard, the inventive TCR, polypeptide, or protein can, for example, consist essentially of the amino acid sequence of SEQ ID NO: 21, SEQ ID NO: 22, SEQ ID NO: 23, SEQ ID NO: 24, both of SEQ ID NOs: 21-22 or both of SEQ ID NO: 23-24. Also, for instance, the inventive TCRs, polypeptides, or proteins can consist essentially of the amino acid sequence(s) of (i) SEQ ID NO: 9, (ii) SEQ ID NO: 10, (iii) both of SEQ ID NOs: 9 and 10, (iv) SEQ ID NO: 11, (v) SEQ ID NO: 12, or (vi) both of SEQ ID NO: 11 and 12. Furthermore, the inventive TCRs, polypeptides, or proteins can consist essentially of the amino acid sequences of (a)

any one or more of SEQ ID NOs: 3-8; (b) all of SEQ ID NO: 3-5; (c) all of SEQ ID NO: 6-8; or (d) all of SEQ ID NOs: 3-8.

The TCRs, polypeptides, and proteins of the invention can be of any length, i.e., can comprise any number of amino acids, provided that the TCRs, polypeptides, or proteins retain their biological activity, e.g., the ability to specifically bind to EGFR E746_A750del; detect cancer in a mammal; or treat or prevent cancer in a mammal, etc. For example, the polypeptide can be in the range of from about 50 to about 5000 amino acids long, such as about 50, about 70, about 75, about 100, about 125, about 150, about 175, about 200, about 300, about 400, about 500, about 600, about 700, about 800, about 900, about 1000 or more amino acids in length. In this regard, the polypeptides of the invention also include oligopeptides.

The TCRs, polypeptides, and proteins of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention can be obtained by methods known in the art such as, for example, de novo synthesis. Also, polypeptides and proteins can be recombinantly produced using the nucleic acids described herein using standard recombinant methods. See, for instance, Green and Sambrook, *Molecular Cloning: A Laboratory Manual*, 4$^{th}$ ed., Cold Spring Harbor Press, Cold Spring Harbor, NY (2012). Alternatively, the TCRs, polypeptides, and/or proteins described herein can be commercially synthesized by companies, such as Synpep (Dublin, CA), Peptide Technologies Corp. (Gaithersburg, MD), and Multiple Peptide Systems (San Diego, CA). In this respect, the inventive TCRs, polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art.

An embodiment of the invention provides a nucleic acid comprising a nucleotide sequence encoding any of the TCRs, polypeptides, or proteins described herein. "Nucleic acid," as used herein, includes "polynucleotide," "oligonucleotide," and "nucleic acid molecule," and generally means a polymer of DNA or RNA, which can be single-stranded or double-stranded, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methyl guanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, CO) and Synthegen (Houston, TX).

The nucleic acid can comprise any nucleotide sequence which encodes any of the TCRs, polypeptides, or proteins described herein. In an embodiment of the invention, the nucleic acid may comprise the nucleotide sequences of any one of SEQ ID NOs: 26-29 (Table 4). In an embodiment of the invention, the nucleic acid comprises the nucleotide sequences of both of SEQ ID NOs: 26-27 or both of SEQ ID NO: 28-29.

TABLE 4

| SEQ ID NO: 26 | WT human alpha chain |
| SEQ ID NO: 27 | WT human β chain |
| SEQ ID NO: 28 | cysteine-substituted, LVL-modified TCR α chain |
| SEQ ID NO: 29 | cysteine-substituted, LVL-modified TCR β chain |

In an embodiment of the invention, the nucleic acid comprises a codon-optimized nucleotide sequence encoding any of the TCRs, polypeptides, or proteins described herein. Without being bound to any particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency. For example, SEQ ID NOs: 28-29 are codon optimized for expression in human cells.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein. In this regard, the nucleic acid may consist essentially of any of the nucleotide sequences described herein.

The nucleic acids of the invention can be incorporated into a recombinant expression vector. In this regard, the invention provides a recombinant expression vector comprising any of the nucleic acids of the invention. In an embodiment of the invention, the recombinant expression vector comprises a nucleotide sequence encoding the α chain, the β chain, and linker peptide.

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector. In an especially preferred embodiment, the recombinant expression vector is an MSGV1 vector.

The recombinant expression vectors of the invention can be prepared using standard recombinant DNA techniques described in, for example, Green and Sambrook et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein, or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, nitroreductase, and the inducible caspase 9 gene system.

In an embodiment of the invention, the recombinant expression vector comprises a nucleotide sequence encoding the α chain, the β chain, and linker peptide. For example, in an embodiment, the recombinant expression vector comprises a nucleotide sequence encoding the full-length alpha and beta chains of the inventive TCR, polypeptide, or protein with a linker positioned between them. In an embodiment, the recombinant expression vector comprises a nucleotide sequence encoding an alpha chain and a beta chain of any of the TCRs, polypeptides, or proteins described herein, wherein the nucleotide sequence encoding the beta chain is positioned 5' of the nucleotide sequence encoding the alpha chain. In this regard, the nucleotide sequence encoding the alpha chain may be positioned 3' of the nucleotide sequence encoding the beta chain. Examples of nucleotide sequences, wherein the nucleotide sequence encoding the beta chain is positioned 5' of the nucleotide sequence encoding the alpha chain include SEQ ID NO: 31 (expression cassette) and SEQ ID NO: 33 (MSGVI vector including the expression cassette).

In another embodiment, the nucleotide sequence encoding the beta chain is positioned 3' of the nucleotide sequence encoding the alpha chain. In this regard, the nucleotide sequence encoding the alpha chain may be positioned 5' of the nucleotide sequence encoding the beta chain. Examples of nucleotide sequences, wherein the nucleotide sequence encoding the alpha chain is positioned 5' of the nucleotide sequence encoding the beta chain include SEQ ID NO: 30 (expression cassette) and SEQ ID NO: 32 (MSGVI vector including the expression cassette).

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5a cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD4$^+$ T cells, CD8$^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990). In an embodiment, expansion of the numbers of T cells is carried out by culturing the T cells with OKT3 antibody, IL-2, and feeder PBMC (e.g., irradiated allogeneic PBMC).

The inventive TCRs, polypeptides, proteins, nucleic acids, recombinant expression vectors, and host cells (including populations thereof), can be isolated and/or purified. The term "isolated," as used herein, means having been removed from its natural environment. The term "purified," as used herein, means having been increased in purity, wherein "purity" is a relative term, and not to be necessarily construed as absolute purity. For example, the purity can be at least about 50%, can be greater than about 60%, about 70%, about 80%, about 90%, about 95%, or can be about 100%.

The inventive TCRs, polypeptides, proteins, nucleic acids, recombinant expression vectors, and host cells (including populations thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, nucleic acids, expression vectors, and host cells (including populations thereof), described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Methods for preparing administrable compositions are known or apparent to those skilled in the art and are described in more detail in, for example, *Remington: The Science and Practice of Pharmacy*, $22^{nd}$ Ed., Pharmaceutical Press (2012). It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell (or population thereof) expressing the inventive TCR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen (e.g., EGFR E746_A750del), or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which each is given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the cancer being treated. In an embodiment in which the inventive TCR material is a population of cells, the number of cells administered per infusion may vary, e.g., from about $1 \times 10^6$ to about $1 \times 10^{12}$ cells or more. In certain embodiments, fewer than $1 \times 10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a chemotherapeutic agent. The practice of conjugating compounds to a chemotherapeutic agent is known in the art. One of ordinary skill in the art recognizes that sites on the inventive TCR materials, which are not necessary for the function of the inventive TCR materials, are suitable sites for attaching a bridge and/or a chemotherapeutic agent, provided that the bridge and/or chemotherapeutic agent, once attached to the inventive TCR materials, do(es) not interfere with the function of the inventive TCR materials, i.e., the ability to bind to EGFR E746_A750del or to detect, treat, or prevent cancer.

It is contemplated that the inventive pharmaceutical compositions, TCRs, polypeptides, proteins, nucleic acids, recombinant expression vectors, host cells, and populations of cells can be used in methods of treating or preventing cancer. Without being bound to a particular theory, the inventive TCRs are believed to bind specifically to EGFR E746_A750del, such that the TCR (or related inventive polypeptide or protein), when expressed by a cell, is able to mediate an immune response against a target cell expressing EGFR E746_A750del. In this regard, the invention provides a method of treating or preventing cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, for use in the treatment or prevention of cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof. Alternatively or additionally, "prevention" may encompass preventing or delaying the recurrence of cancer, or a symptom or condition thereof.

Also provided is a method of detecting the presence of cancer in a mammal. The method comprises (i) contacting a sample comprising one or more cells from the mammal with any of the inventive TCRs, polypeptides, proteins, nucleic acids, recombinant expression vectors, host cells, populations of cells, or pharmaceutical compositions described herein, thereby forming a complex, and (ii) detecting the complex, wherein detection of the complex is indicative of the presence of cancer in the mammal.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive method of detecting cancer, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, or populations of cells, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, colorectal cancer, endometrial cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is lung cancer. Preferably, the lung cancer is NSCLC. In an embodiment of the invention, the cancer is a cancer which expresses a mutated EGFR amino acid sequence with a deletion of amino acid residues 746-750, wherein amino acid residues 746-750 are defined by reference to SEQ ID NO: 1.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

Example 1

This example demonstrates the isolation of a TCR having antigenic specificity for the mutated human EGFR amino acid sequence of AIKTSPKANKEIL (SEQ ID NO: 36).

TIL were isolated from a NSCLC patient. T cells which recognize EGFR E746_A750del were isolated from the TIL. Nucleotide sequences which encode the full length alpha and beta chains (SEQ ID NOs: 26-27, respectively) were isolated from the anti-EGFR E746_A750del T cells by single cell reverse transcription polymerase chain reaction (RT-PCR). The amino acid sequences of the TCR are set forth in Table 5.

TABLE 5

| TCR Component | Sequence |
|---|---|
| CDR1 α (SEQ ID NO: 3) | SSVPPY |
| CDR2 α (SEQ ID NO: 4) | YTSAATLV |
| CDR3 α (SEQ ID NO: 5) | CAVSEDSNYQLIW |
| CDR1 β (SEQ ID NO: 6) | GTSNPN |
| CDR2 β (SEQ ID NO: 7) | SVGIG |
| CDR3 β (SEQ ID NO: 8) | CAYSPGLASDTQYF |
| variable region α (SEQ ID NO: 9) | MLLLLVPVLEVIFTLGGTRAQSV TQLGSHVSVSEGALVLLRCNYSS SVPPYLFWYVQYPNQGLQLLLKY TSAATLVKGINGFEAEFKKSETS |

TABLE 5-continued

| TCR Component | Sequence |
|---|---|
| | FHLTKPSAHMSDAAEYFCAVSED<br>SNYQLIWGAGTKLIIKP |
| variable region β<br>(SEQ ID NO: 10) | MLCSLLALLLGTFFGVRSQTIHQ<br>WPATLVQPVGSPLSLECTVEGTS<br>NPNLYWYRQAAGRGLQLLFYSVG<br>IGQISSEVPQNLSASRPQDRQFI<br>LSSKKLLLSDSGFYLCAYSPGLA<br>SDTQYFGPGTRLTVL |
| Full-length alpha<br>chain amino<br>acid sequence | SEQ ID NO: 19 |
| Full-length beta<br>chain amino<br>acid sequence | SEQ ID NO: 20 |

Example 2

This example demonstrates the construction of a retroviral vector encoding the TCR of Example 1 with the modifications described in this Example.

To facilitate cloning of the TCR expression cassette into the MSGV1 vector site, an alanine was inserted into the second position of each the alpha and the beta chains, resulting in the alpha and beta chain variable region amino acid sequences of SEQ ID NOs: 11 and 12, respectively.

The human β chain constant region was replaced with the murine β chain constant region. The human α chain constant region was replaced with the murine α chain constant region. Without being bound to a particular theory or mechanism, it is believed that replacing the constant regions of the human TCRα and TCRβ chains with the corresponding murine constant regions improves TCR expression and functionality (Cohen et al., *Cancer Res.,* 66(17): 8878-86 (2006)).

In addition, the murine TCRα and TCRβ constant chains were cysteine-modified. Transmembrane hydrophobic mutations were also introduced into the murine TCRα constant chain. Without being bound to a particular theory or mechanism, it is believed that these modifications result in preferential pairing of the introduced TCR chains and enhanced TCR surface expression and functionality (Cohen et al., *Cancer Res.,* 67(8):3898-903 (2007); Haga-Friedman et al., *J. Immu.,* 188: 5538-5546 (2012)).

After the modifications described in this Example were made, the full-length TCR α chain comprised the amino acid sequence of SEQ ID NO: 23, and the full-length TCR β chain comprised the amino acid sequence of SEQ ID NO: 24.

The nucleotide sequences encoding the modified TCR α and β chains were codon optimized for expression in human cells, resulting in the nucleotide sequences of SEQ ID NO: 28 (codon optimized full-length modified α chain) and SEQ ID NO: 29 (codon-optimized full-length modified β chain).

Nucleotide sequences encoding the modified TCR α and β chains (SEQ ID NOs: 28 and 29) were cloned into an MSGV1 retroviral vector with one of the following two expression cassette configurations: (1) 5'-TCR alpha chain-linker-TCR beta chain-3' (Construct 1; SEQ ID NO: 30) or (2) 5'-TCR beta chain-linker-TCR alpha chain-3' (Construct 2; SEQ ID NO: 31). The P2A linker comprised the amino acid sequence of SEQ ID NO: 25. The vector comprising construct 1 comprised the nucleotide sequence of SEQ ID NO: 32. The vector comprising construct 2 comprised the nucleotide sequence of SEQ ID NO: 33.

Example 3

This example demonstrates that peripheral blood T cells transduced with the modified TCR α and β chain of Example 2 specifically recognize autologous dendritic cells pulsed with mutated EGFR peptide.

Peripheral blood lymphocytes (PBL) were retrovirally transduced as described in one of (1)-(4) below:

1. The cells were transduced with a vector encoding an HLA-A3-restricted KRAS G12V-reactive TCR (irrelevant TCR, negative control);
2. Retrovirus containing a vector encoding the modified TCR alpha chain of Example 2 (SEQ ID NO: 23) and retrovirus containing a vector encoding the modified TCR beta chain of Example 2 (SEQ ID NO: 24) were separately produced and mixed. The cells were transduced with the mixture of retroviruses.
3. The cells were transduced with a vector comprising Construct 1 of Example 2 (alpha chain and beta chain were cloned in the MSGV1 vector in the order of alpha chain-linker-beta chain) (SEQ ID NO: 32).
4. The cells were transduced with a vector comprising Construct 2 of Example 2 (alpha chain and beta chain were cloned in the MSGV1 vector in the order of beta chain-linker-alpha chain) (SEQ ID NO: 33).

The transduced cells were co-cultured with autologous dendritic cells which had been pulsed with 1 μM of the wild-type (WT) EGFR peptide of PEGEKVKIPVAIKEL-REATSPKANK (SEQ ID NO: 34) or the mutated EGFR (E746_A750 del) peptide of PEGEKVKIPVAIKTSP-KANKEILDE (SEQ ID NO: 35). Transduced cells cultured in medium alone served as a control.

IFN-γ secretion was measured. The results are shown in FIG. 1. Each of transductions (2)-(4) above conferred recognition of the mutated EGFR (E746_A750 del) peptide-pulsed autologous dendritic cells. Negative control transduction (1) failed to confer recognition of the mutated EGFR (E746_A750 del) peptide-pulsed autologous dendritic cells. In this experiment, the order of TCR alpha-linker-TCR beta (Construct 1) performed better than the others.

Example 4

This example demonstrates that peripheral blood T cells transduced with the modified TCR α and β chain of Example 2 specifically recognize NSCLC cell lines, which express the E746_A750 deletion, in an HLA-DPA1*02:01, DPB1*01:01-restricted manner.

PC-9 and HCC827 are NSCLC cell lines which express EGFR with the E746_A750 deletion. The cell lines were retrovirally transduced with a combination of (i) HLA-DPA1*01:03 and DPB1*01:01 or (ii) HLA-DPA1*02:01 and DPB1*01:01.

PBL were retrovirally transduced as described in one of (1)-(4) of Example 3.

The transduced cells were co-cultured with each one of the transduced cell lines. Transduced PBL were co-cultured with untransduced cell line as a control.

Figure 2:
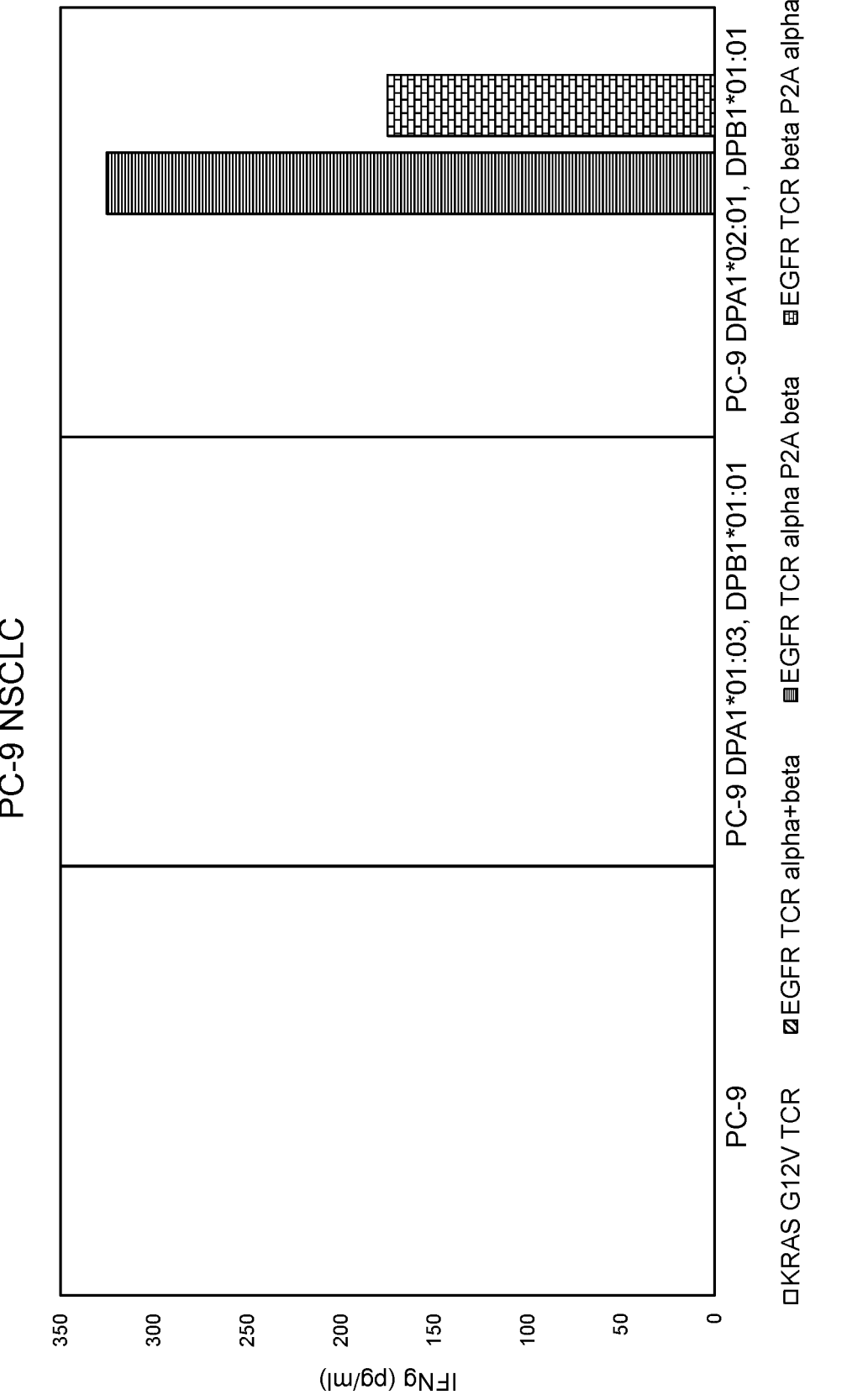
FIG. 2 is a graph showing the amount of IFN-γ (pg/ml) secreted upon co-culture of cells transduced with Construct 1 (EGFR TCR alpha P2A beta), Construct 2 (EGFR TCR beta P2A alpha), an anti-KRAS G12V TCR, or a mixture of vectors encoding the α and β chains (EGFR TCR alpha+ beta) with PC-9 cells which had been retrovirally transduced with a combination of (i) HLA-DPA1*01:03 and DPB1*01: 01 or (ii) HLA-DPA1*02:01 and DPB1*01:01. Transduced PBL were co-cultured with untransduced PC-9 cells as a control.
Figure 3:
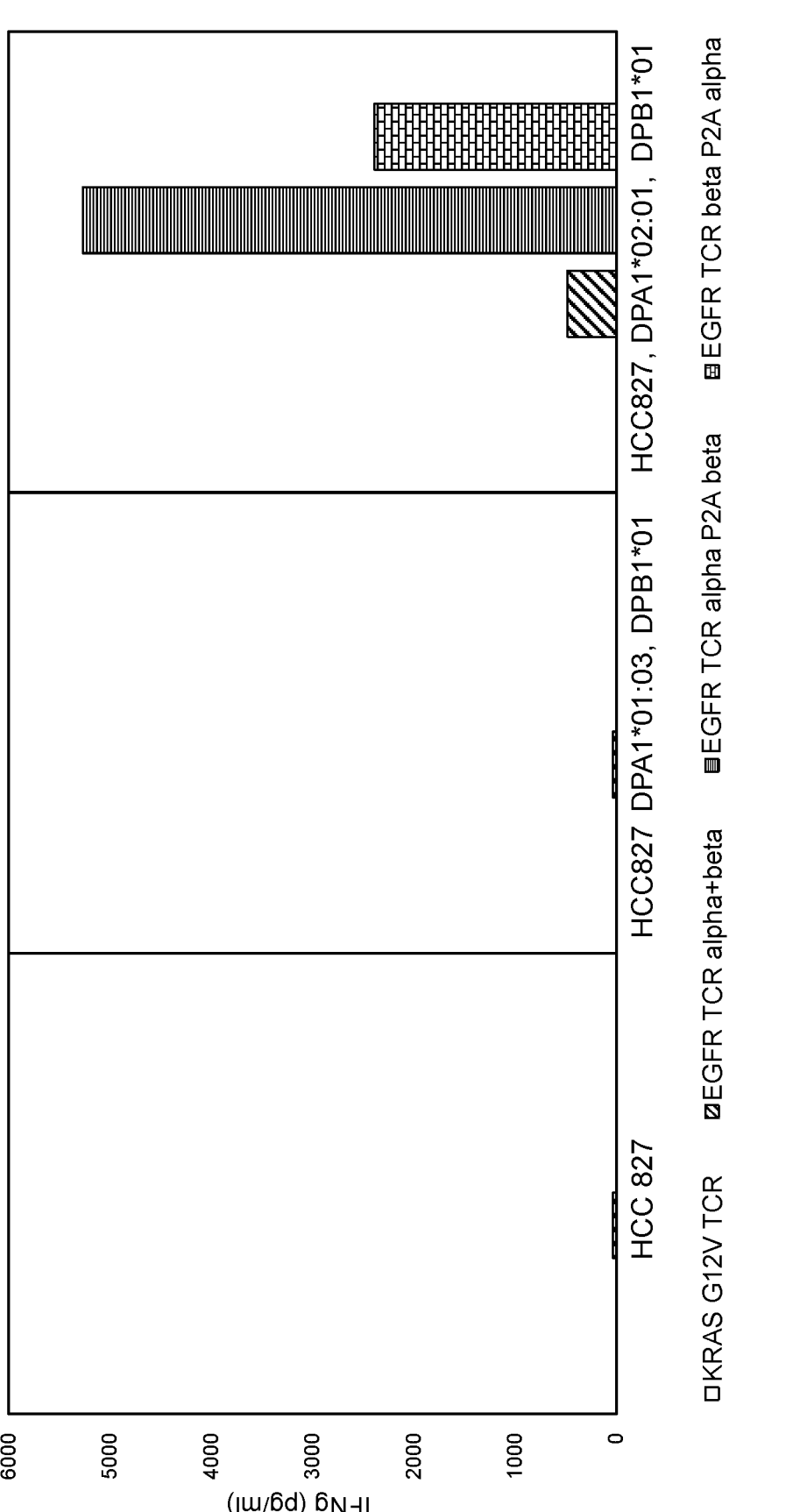
FIG. 3 is a graph showing the amount of IFN-γ (pg/ml) secreted upon co-culture of cells transduced with Construct 1 (EGFR TCR alpha P2A beta), Construct 2 (EGFR TCR beta P2A alpha), an anti-KRAS G12V TCR, or a mixture of vectors encoding the α and β chains (EGFR TCR alpha+ beta) with HCC827 cells which had been retrovirally transduced with a combination of (i) HLA-DPA1*01:03 and DPB1*01:01 or (ii) HLA-DPA1*02:01 and DPB1*01:01. Transduced PBL were co-cultured with untransduced HCC827 cells as a control.

IFN-γ was measured. The results are shown in FIG. 2 (PC-9) and FIG. 3 (HCC827). As shown in FIGS. 2-3, the TCR is HLA-DPA1*02:01, DPB1*01:01-restricted. The T cells transduced with the modified TCR α and β chain of Example 2 specifically recognized NSCLC cell lines, which express the E746_A750 deletion, in an HLA-DPA1*02:01, DPB1*01:01-restricted manner.

Example 5

This example demonstrates that peripheral blood T cells transduced with the modified TCR α and β chain of Example 2 recognize the EGFR E746_A750del peptide of AIKTSP-KANKEIL (SEQ ID NO: 36).

A series of truncated EGFR E746_A750del peptides SEQ ID NOs: 35 and 40-50 (shown in FIG. 4A and Table B) were synthesized. FIG. 4B shows the location of the deleted wild-type EGFR amino acid residues 746-750 (ELREA (SEQ ID NO: 51)) in relation to the mutated EGFR E746_A750del peptide AIKTSPKANKEIL (SEQ ID NO: 36).

TABLE B

| SEQ ID NO: | Peptide |
|---|---|
| 35 | PEGEKVKIPVAIKTSPKANKEILDE |
| 40 | GEKVKIPVAIKTSPKANKEILDE |
| 41 | KVKIPVAIKTSPKANKEILDE |
| 42 | KIPVAIKTSPKANKEILDE |
| 43 | PVAIKTSPKANKEILDE |
| 44 | AIKTSPKANKEILDE |
| 45 | KTSPKANKEILDE |
| 46 | PEGEKVKIPVAIKTSPKANKEIL |
| 47 | PEGEKVKIPVAIKTSPKANKE |
| 48 | PEGEKVKIPVAIKTSPKAN |
| 49 | PEGEKVKIPVAIKTSPK |
| 50 | PEGEKVKIPVAIKTS |

PBL were retrovirally transduced with a vector comprising Construct 1 of Example 2 (alpha chain and beta chain were cloned in the MSGV1 vector in the order of alpha chain-linker-beta chain) (SEQ ID NO: 32). The transduced cells were co-cultured with autologous dendritic cells which had been pulsed with 1 µM of one of the EGFR E746_A750del peptides of SEQ ID NOs: 35 and 40-50. IFN-γ was measured. The results are shown in FIG. 4A.

Figure 4A:
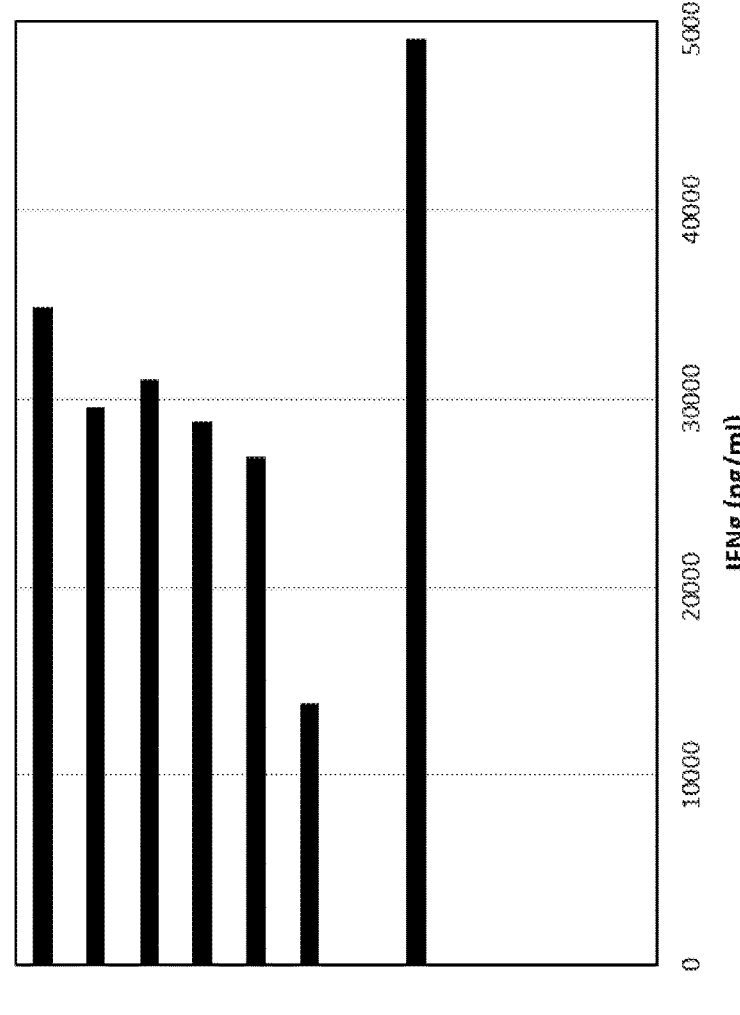
FIG. 4A is a graph showing the amount of IFN-γ (pg/ml) secreted upon co-culture of cells transduced with Construct 1 (5'-TCR alpha chain-linker-TCR beta chain-3') (SEQ ID NO: 30) with dendritic cells which had been pulsed with one of the mutated EGFR (E746_A750 del) peptides of SEQ ID NOs: 35 and 40-50.
Figure 4B:
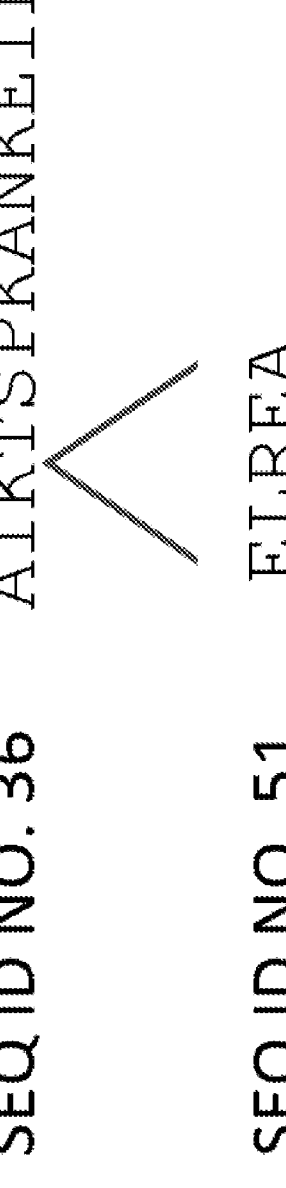
FIG. 4B is a schematic showing the location of the deleted wild-type EGFR amino acid residues 746-750 (ELREA (SEQ ID NO: 51)) in relation to the mutated EGFR E746_A750del peptide AIKTSPKANKEIL (SEQ ID NO: 36).

As shown in FIG. 4A, the shortest peptide recognized by the transduced cells was AIKTSPKANKEILDE (SEQ ID NO: 44). When the N-terminal AI is removed (see KTSP-KANKEILDE (SEQ ID NO: 45), recognition was lost. The peptide PEGEKVKIPVAIKTSPKANKEIL (SEQ ID NO: 46) was also recognized by the transduced cells. But when the C-terminal "IL" were removed (see PEGEKVKIPVAI-KTSPKANKE (SEQ ID NO: 47)), recognition was lost.

Based on these data, the TCR epitope was narrowed down to the 13-mer peptide of AIKTSPKANKEIL (SEQ ID NO: 36). It is believed that there are four possibilities for the minimal epitope: AIKTSPKANKEIL (SEQ ID NO: 36), AIKTSPKANKEI (SEQ ID NO: 37), IKTSPKANKEIL (SEQ ID NO: 38), and IKTSPKANKEI (SEQ ID NO: 39). So, the minimal epitope may be as short as 11 amino acids.

Although the minimal epitope may provide the minimum sequence for recognition, the minimal peptide might not provide the strongest recognition. As shown in FIG. 4A, the N-terminal PV of PVAIKTSPKANKEILDE (SEQ ID NO: 43) is not necessary for recognition, but removing PV lowers the recognition (see AIKTSPKANKEILDE (SEQ ID NO: 44). Without being bound to a particular theory or mechanism, it is believed that the N-terminal PV of PVAIKTSP-KANKEILDE (SEQ ID NO: 43) may contribute to the recognition by the TCR.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified T cell receptor (TCR) having antigenic specificity for a peptide comprising the mutated epidermal growth factor receptor (EGFR) amino acid sequence of AIKTSPKANKEIL (SEQ ID NO: 36) presented by a human leukocyte antigen (HLA) Class II molecule that is a heterodimer of an HLA-DPA1*02:01 chain and an HLA-DPB1*01:01 chain, wherein the TCR comprises an α chain comprising an α chain complementarity determining region (CDR) 1 comprising the amino acid sequence of SEQ ID NO: 3, an α chain CDR2 comprising the amino acid sequence of SEQ ID NO: 4, and an α chain CDR3 comprising the amino acid sequence of SEQ ID NO: 5; and a β chain comprising a β chain CDR1 comprising the amino acid sequence of SEQ ID NO: 6, a β chain CDR2 comprising the amino acid sequence of SEQ ID NO: 7, and a β chain CDR3 comprising the amino acid sequence of SEQ ID NO: 8.

2. The TCR of claim 1 wherein:

(a) the α chain comprises an amino acid sequence at least 99% identical to the amino acid sequence of SEQ ID NO: 9;

(b) the β chain comprises an amino acid sequence at least 99% identical to the amino acid sequence of SEQ ID NO: 10;

(c) the α chain comprises an amino acid sequence at least 99% identical to the amino acid sequence of SEQ ID NO: 11;

(d) the β chain comprises an amino acid sequence at least 99% identical to the amino acid sequence of SEQ ID NO: 12;

(e) the α chain comprises an amino acid sequence at least 99% identical to amino acids 21-132 of SEQ ID NO: 9;

(f) the β chain comprises an amino acid sequence at least 99% identical to amino acids 19-130 of SEQ ID NO: 10;

(g) the α chain comprises an amino acid sequence at least 99% identical to amino acids 22-133 of SEQ ID NO: 11;

(h) the β chain comprises an amino acid sequence at least 99% identical to amino acids 20-131 of SEQ ID NO:12; or (i) both (a) and (b); both (c) and (d); both (e) and (f); both (g) and (h); both (a) and (f); both (b) and (e); both (c) and (h); or both (d) and (g).

3. The TCR of claim 1, wherein:

(a) the α chain comprises a constant region comprising an amino acid sequence at least 99% identical to the amino acid sequence of SEQ ID NO: 15, wherein:

(i) X at position 48 of SEQ ID NO: 15 is Thr or Cys;

(ii) X at position 112 of SEQ ID NO: 15 is Ser, Ala, Val, Leu, Ile, Pro, Phe, Met, or Trp;

(iii) X at position 114 of SEQ ID NO: 15 is Met, Ala, Val, Leu, Ile, Pro, Phe, or Trp; and (iv) X at position 115 of SEQ ID NO: 15 is Gly, Ala, Val, Leu, Ile, Pro, Phe, Met, or Trp;

(b) the β chain comprises a constant region comprising an amino acid sequence at least 99% identical to the amino acid sequence of SEQ ID NO: 16, wherein X at position 57 of SEQ ID NO: 16 is Ser or Cys; or (c) both (a) and (b).

4. The TCR of claim 1, wherein:

(a) the α chain comprises an amino acid sequence at least 99% identical to the amino acid sequence of SEQ ID NO: 21, wherein:

(i) X at position 181 of SEQ ID NO: 21 is Thr or Cys;

(ii) X at position 245 of SEQ ID NO: 21 is Ser, Ala, Val, Leu, Ile, Pro, Phe, Met, or Trp;

(iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp;

(b) the β chain comprises an amino acid sequence at least 99% identical to the amino acid sequence of SEQ ID NO: 22, wherein X at position 188 of SEQ ID NO: 22 is Ser or Cys;

(c) the α chain comprises an amino acid sequence at least 99% identical to amino acids 22-270 of SEQ ID NO: 21, wherein:

(i) X at position 181 of SEQ ID NO: 21 is Thr or Cys;

(ii) X at position 245 of SEQ ID NO: 21 is Ser, Ala, Val, Leu, Ile, Pro, Phe, Met, or Trp;

(iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp;

(d) the β chain comprises an amino acid sequence at least 99% identical to amino acids 20-304 of SEQ ID NO: 22, wherein X at position 188 of SEQ ID NO: 22 is Ser or Cys; or (e) both (a) and (b); both (c) and (d); both (a) and (d); or both (b) and (c).

5. The TCR of claim 1 wherein:

(a) the α chain comprises the amino acid sequence of SEQ ID NO: 9;

(b) the β chain comprises the amino acid sequence of SEQ ID NO: 10;

(c) the α chain comprises the amino acid sequence of SEQ ID NO: 11;

(d) the β chain comprises the amino acid sequence of SEQ ID NO: 12;

(e) the α chain comprises amino acids 21-132 of SEQ ID NO: 9;

(f) the β chain comprises amino acids 19-130 of SEQ ID NO: 10;

(g) the α chain comprises amino acids 22-133 of SEQ ID NO: 11;

(h) the β chain comprises amino acids 20-131 of SEQ ID NO: 12; or (i) both (a) and (b); both (c) and (d); both (e) and (f); both (g) and (h); both (a) and (f);

both (b) and (e); both (c) and (h); or both (d) and (g).

6. The TCR of claim 1, further comprising:

(a) an α chain constant region comprising the amino acid sequence of SEQ ID NO: 15, wherein:

(i) X at position 48 of SEQ ID NO: 15 is Thr or Cys;

(ii) X at position 112 of SEQ ID NO: 15 is Ser, Ala, Val, Leu, Ile, Pro, Phe, Met, or Trp;

(iii) X at position 114 of SEQ ID NO: 15 is Met, Ala, Val, Leu, Ile, Pro, Phe, or Trp; and (iv) X at position 115 of SEQ ID NO: 15 is Gly, Ala, Val, Leu, Ile, Pro, Phe, Met, or Trp;

(b) a β chain constant region comprising the amino acid sequence of SEQ ID NO: 16, wherein X at position 57 of SEQ ID NO: 16 is Ser or Cys; or (c) both (a) and (b).

7. The TCR of claim 1, wherein:

(a) the α chain comprises the amino acid sequence of SEQ ID NO: 21, wherein:

(i) X at position 181 of SEQ ID NO: 21 is Thr or Cys;

(ii) X at position 245 of SEQ ID NO: 21 is Ser, Ala, Val, Leu, Ile, Pro, Phe, Met, or Trp;

(iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp;

(b) the β chain comprises the amino acid sequence of SEQ ID NO: 22, wherein X at position 188 of SEQ ID NO: 22 is Ser or Cys;

(c) the α chain comprises amino acids 22-270 of SEQ ID NO: 21, wherein:

(i) X at position 181 of SEQ ID NO: 21 is Thr or Cys;

(ii) X at position 245 of SEQ ID NO: 21 is Ser, Ala, Val, Leu, Ile, Pro, Phe, Met, or Trp;

(iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp;

(d) the β chain comprises amino acids 20-304 of SEQ ID NO: 22, wherein X at position 188 of SEQ ID NO: 22 is Ser or Cys; or (e) both (a) and (b); both (c) and (d); both (a) and (d); or both (b) and (c).

8. An isolated or purified polypeptide comprising a functional portion of the TCR of claim 1, wherein the functional portion has antigenic specificity for the mutated EGFR amino acid sequence of AIKTSPKANKEIL (SEQ ID NO: 36) presented by an HLA Class II molecule that is a heterodimer of an HLA-DPA1*02:01 chain and an HLA-DPB1*01:01 chain, and wherein the functional portion comprises a TCR α chain comprising an α chain CDR1 comprising the amino acid sequence of SEQ ID NO: 3, an α chain CDR2 comprising the amino acid sequence of SEQ ID NO: 4, and an α chain CDR3 comprising the amino acid sequence of SEQ ID NO: 5; and a TCR β chain comprising a β chain CDR1 comprising the amino acid sequence of SEQ ID NO: 6, a β chain CDR2 comprising the amino acid sequence of SEQ ID NO: 7, and a β chain CDR3 comprising the amino acid sequence of SEQ ID NO: 8.

9. The isolated or purified polypeptide according to claim 8, wherein:

(a) the α chain of the functional portion comprises an amino acid sequence at least 99% identical to the amino acid sequence of SEQ ID NO: 9;

(b) the β chain of the functional portion comprises an amino acid sequence at least 99% identical to the amino acid sequence of SEQ ID NO: 10;

(c) the α chain of the functional portion comprises an amino acid sequence at least 99% identical to the amino acid sequence of SEQ ID NO: 11;

(d) the β chain of the functional portion comprises an amino acid sequence at least 99% identical to the amino acid sequence of SEQ ID NO: 12;

(e) the α chain of the functional portion comprises an amino acid sequence at least 99% identical to amino acids 21-132 of SEQ ID NO: 9;

(f) the β chain of the functional portion comprises an amino acid sequence at least 99% identical to amino acids 19-130 of SEQ ID NO: 10;

(g) the α chain of the functional portion comprises an amino acid sequence at least 99% identical to amino acids 22-133 of SEQ ID NO: 11;

(h) the β chain of the functional portion comprises an amino acid sequence at least 99% identical to amino acids 20-131 of SEQ ID NO: 12; or (i) both (a) and (b); both (c) and (d); both (e) and (f); both (g) and (h); both (a) and (f); both (b) and (e); both (c) and (h); or both (d) and (g).

10. The isolated or purified polypeptide of claim 8, wherein:

(a) the α chain of the functional portion further comprises an amino acid sequence at least 99% identical to the amino acid sequence of SEQ ID NO: 15, wherein:

(i) X at position 48 of SEQ ID NO: 15 is Thr or Cys;

(ii) X at position 112 of SEQ ID NO: 15 is Ser, Ala, Val, Leu, Ile, Pro, Phe, Met, or Trp;

(iii) X at position 114 of SEQ ID NO: 15 is Met, Ala, Val, Leu, Ile, Pro, Phe, or Trp; and (iv) X at position 115 of SEQ ID NO: 15 is Gly, Ala, Val, Leu, Ile, Pro, Phe, Met, or Trp;

(b) the β chain of the functional portion further comprises an amino acid sequence at least 99% identical to the amino acid sequence of SEQ ID NO: 16, wherein X at position 57 of SEQ ID NO: 16 is Ser or Cys; or (c) both (a) and (b).

11. The isolated or purified polypeptide of claim 8, wherein:

(a) the α chain of the functional portion comprises an amino acid sequence at least 99% identical to the amino acid sequence of SEQ ID NO: 21, wherein:

(i) X at position 181 of SEQ ID NO: 21 is Thr or Cys;

(ii) X at position 245 of SEQ ID NO: 21 is Ser, Ala, Val, Leu, Ile, Pro, Phe, Met, or Trp;

(iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp;

(b) the β chain of the functional portion comprises an amino acid sequence at least 99% identical to the amino acid sequence of SEQ ID NO: 22, wherein X at position 188 of SEQ ID NO: 22 is Ser or Cys;

(c) the α chain of the functional portion comprises an amino acid sequence at least 99% identical to amino acids 22-270 of SEQ ID NO: 21, wherein:

(i) X at position 181 of SEQ ID NO: 21 is Thr or Cys;

(ii) X at position 245 of SEQ ID NO: 21 is Ser, Ala, Val, Leu, Ile, Pro, Phe, Met, or Trp;

(iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp;

(d) the β chain of the functional portion comprises an amino acid sequence at least 99% identical to amino acids 20-304 of SEQ ID NO: 22, wherein X at position 188 of SEQ ID NO: 22 is Ser or Cys; or (e) both (a) and (b); both (c) and (d); both (a) and (d); or both (b) and (c).

12. The isolated or purified polypeptide according to claim 8, wherein:

(a) the α chain of the functional portion comprises the amino acid sequence of SEQ ID NO: 9;

(b) the β chain of the functional portion comprises the amino acid sequence of SEQ ID NO: 10;

(c) the α chain of the functional portion comprises the amino acid sequence of SEQ ID NO: 11;

(d) the β chain of the functional portion comprises the amino acid sequence of SEQ ID NO: 12;

(e) the α chain of the functional portion comprises amino acids 21-132 of SEQ ID NO: 9;

(f) the β chain of the functional portion comprises amino acids 19-130 of SEQ ID NO: 10;

(g) the α chain of the functional portion comprises amino acids 22-133 of SEQ ID NO: 11;

(h) the β chain of the functional portion comprises amino acids 20-131 of SEQ ID NO: 12; or (i) both (a) and (b); both (c) and (d); both (e) and (f); both (g) and (h); both (a) and (f); both (b) and (e); both (c) and (h); or both (d) and (g).

13. The isolated or purified polypeptide of claim 8, wherein:

(a) the α chain of the functional portion further comprises the amino acid sequence of SEQ ID NO: 15, wherein:

(i) X at position 48 of SEQ ID NO: 15 is Thr or Cys;

(ii) X at position 112 of SEQ ID NO: 15 is Ser, Ala, Val, Leu, Ile, Pro, Phe, Met, or Trp;

(iii) X at position 114 of SEQ ID NO: 15 is Met, Ala, Val, Leu, Ile, Pro, Phe, or Trp; and (iv) X at position 115 of SEQ ID NO: 15 is Gly, Ala, Val, Leu, Ile, Pro, Phe, Met, or Trp;

(b) the β chain of the functional portion further comprises the amino acid sequence of SEQ ID NO: 16, wherein X at position 57 of SEQ ID NO: 16 is Ser or Cys; or (c) both (a) and (b).

14. The isolated or purified polypeptide of claim 8, wherein:

(a) the α chain of the functional portion comprises the amino acid sequence of SEQ ID NO: 21, wherein:

(i) X at position 181 of SEQ ID NO: 21 is Thr or Cys;

(ii) X at position 245 of SEQ ID NO: 21 is Ser, Ala, Val, Leu, Ile, Pro, Phe, Met, or Trp;

(iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp;

(b) the β chain of the functional portion comprises the amino acid sequence of SEQ ID NO: 22, wherein X at position 188 of SEQ ID NO: 22 is Ser or Cys;

(c) the α chain of the functional portion comprises amino acids 22-270 of SEQ ID NO: 21, wherein:

(i) X at position 181 of SEQ ID NO: 21 is Thr or Cys;

(ii) X at position 245 of SEQ ID NO: 21 is Ser, Ala, Val, Leu, Ile, Pro, Phe, Met, or Trp;

(iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp;

(d) the β chain of the functional portion comprises amino acids 20-304 of SEQ ID NO: 22, wherein X at position 188 of SEQ ID NO: 22 is Ser or Cys; or (e) both (a) and (b); both (c) and (d); both (a) and (d); or both (b) and (c).

15. An isolated or purified protein having antigenic specificity for a peptide comprising the mutated epidermal growth factor receptor (EGFR) amino acid sequence of AIKTSP-KANKEIL (SEQ ID NO: 36) presented by a human leukocyte antigen (HLA) Class II molecule that is a heterodimer of an HLA-DPA1*02:01 chain and an HLA-DPB1*01:01 chain, wherein the protein comprises a first polypeptide chain comprising a T cell receptor (TCR) a chain amino acid sequence comprising an α chain complementarity determining region (CDR) 1 comprising the amino acid sequence of SEQ ID NO: 3, an α chain CDR2 comprising the amino acid sequence of SEQ ID NO: 4, and an α chain CDR3 comprising the amino acid sequence of SEQ ID NO: 5; and a second polypeptide chain comprising a TCR β chain amino acid sequence comprising a β chain CDR1 comprising the amino acid sequence of SEQ ID NO: 6, a β chain CDR2 comprising the amino acid sequence of SEQ ID NO: 7, and a β chain CDR3 comprising the amino acid sequence of SEQ ID NO: 8.

16. The isolated or purified protein according to claim 15, wherein:

(a) the first polypeptide chain comprises an amino acid sequence at least 99% identical to the amino acid sequence of SEQ ID NO: 9;

(b) the second polypeptide chain comprises an amino acid sequence at least 99% identical to the amino acid sequence of SEQ ID NO: 10;

(c) the first polypeptide chain comprises an amino acid sequence at least 99% identical to the amino acid sequence of SEQ ID NO: 11;

(d) the second polypeptide chain comprises an amino acid sequence at least 99% identical to the amino acid sequence of SEQ ID NO: 12;

(e) the first polypeptide chain comprises an amino acid sequence at least 99% identical to amino acids 21-132 of SEQ ID NO: 9;

(f) the second polypeptide chain comprises an amino acid sequence at least 99% identical to amino acids 19-130 of SEQ ID NO: 10;

(g) the first polypeptide chain comprises an amino acid sequence at least 99% identical to amino acids 22-133 of SEQ ID NO: 11;

(h) the second polypeptide chain comprises an amino acid sequence at least 99% identical to amino acids 20-131 of SEQ ID NO: 12; or (i) both (a) and (b); both (c) and (d); both (e) and (f); both (g) and (h); both (a) and (f); both (b) and (e); both (c) and (h); or both (d) and (g).

17. The isolated or purified protein of claim 15, wherein:

(a) the first polypeptide chain comprises an amino acid sequence at least 99% identical to the amino acid sequence of SEQ ID NO: 15, wherein:

(i) X at position 48 of SEQ ID NO: 15 is Thr or Cys;

(ii) X at position 112 of SEQ ID NO: 15 is Ser, Ala, Val, Leu, Ile, Pro, Phe, Met, or Trp;

(iii) X at position 114 of SEQ ID NO: 15 is Met, Ala, Val, Leu, Ile, Pro, Phe, or Trp; and (iv) X at position 115 of SEQ ID NO: 15 is Gly, Ala, Val, Leu, Ile, Pro, Phe, Met, or Trp;

(b) the second polypeptide chain comprises an amino acid sequence at least 99% identical to the amino acid sequence of SEQ ID NO: 16, wherein X at position 57 of SEQ ID NO: 16 is Ser or Cys; or (c) both (a) and (b).

18. The isolated or purified protein of claim 15, wherein:

(a) the first polypeptide chain comprises an amino acid sequence at least 99% identical to the amino acid sequence of SEQ ID NO: 21, wherein:

(i) X at position 181 of SEQ ID NO: 21 is Thr or Cys;

(ii) X at position 245 of SEQ ID NO: 21 is Ser, Ala, Val, Leu, Ile, Pro, Phe, Met, or Trp;

(iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp;

(b) the second polypeptide chain comprises an amino acid sequence at least 99% identical to the amino acid sequence of SEQ ID NO: 22, wherein X at position 188 of SEQ ID NO: 22 is Ser or Cys;

(c) the first polypeptide chain comprises an amino acid sequence at least 99% identical to amino acids 22-270 of SEQ ID NO: 21, wherein:

(i) X at position 181 of SEQ ID NO: 21 is Thr or Cys;

(ii) X at position 245 of SEQ ID NO: 21 is Ser, Ala, Val, Leu, Ile, Pro, Phe, Met, or Trp;

(iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp;

(d) the second polypeptide chain comprises an amino acid sequence at least 99% identical to amino acids 20-304 of SEQ ID NO: 22, wherein X at position 188 of SEQ ID NO: 22 is Ser or Cys; or (e) both (a) and (b); both (c) and (d); both (a) and (d); or both (b) and (c).

19. The isolated or purified protein according to claim 15, wherein:

(a) the first polypeptide chain comprises the amino acid sequence of SEQ ID NO: 9;

(b) the second polypeptide chain comprises the amino acid sequence of SEQ ID NO: 10;

(c) the first polypeptide chain comprises the amino acid sequence of SEQ ID NO: 11;

(d) the second polypeptide chain comprises the amino acid sequence of SEQ ID NO: 12;

(e) the first polypeptide chain comprises amino acids 21-132 of SEQ ID NO: 9;

(f) the second polypeptide chain comprises amino acids 19-130 of SEQ ID NO: 10;

(g) the first polypeptide chain comprises amino acids 22-133 of SEQ ID NO: 11;

(h) the second polypeptide chain comprises amino acids 20-131 of SEQ ID NO: 12; or (i) both (a) and (b); both (c) and (d); both (e) and (f); both (g) and (h); both (a) and (f); both (b) and (e); both (c) and (h); or both (d) and (g).

20. The isolated or purified protein of claim 15, wherein:

(a) the first polypeptide chain comprises the amino acid sequence of SEQ ID NO: 15, wherein:

(i) X at position 48 of SEQ ID NO: 15 is Thr or Cys;

(ii) X at position 112 of SEQ ID NO: 15 is Ser, Ala, Val, Leu, Ile, Pro, Phe, Met, or Trp;

(iii) X at position 114 of SEQ ID NO: 15 is Met, Ala, Val, Leu, Ile, Pro, Phe, or Trp; and (iv) X at position 115 of SEQ ID NO: 15 is Gly, Ala, Val, Leu, Ile, Pro, Phe, Met, or Trp;

(b) the second polypeptide chain comprises the amino acid sequence of SEQ ID NO: 16, wherein X at position 57 of SEQ ID NO: 16 is Ser or Cys; or (c) both (a) and (b).

21. The isolated or purified protein of claim 15, wherein:

(a) the first polypeptide chain comprises the amino acid sequence of SEQ ID NO: 21, wherein:

(i) X at position 181 of SEQ ID NO: 21 is Thr or Cys;

(ii) X at position 245 of SEQ ID NO: 21 is Ser, Ala, Val, Leu, Ile, Pro, Phe, Met, or Trp;

(iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp;

(b) the second polypeptide chain comprises the amino acid sequence of SEQ ID NO: 22, wherein X at position 188 of SEQ ID NO: 22 is Ser or Cys;

(c) the first polypeptide chain comprises amino acids 22-270 of SEQ ID NO: 21, wherein:

(i) X at position 181 of SEQ ID NO: 21 is Thr or Cys;

(ii) X at position 245 of SEQ ID NO: 21 is Ser, Ala, Val, Leu, Ile, Pro, Phe, Met, or Trp;

(iii) X at position 247 of SEQ ID NO: 21 is Met, Ala, Val, Leu, Ile, Pro, Phe, or Trp; and (iv) X at position 248 of SEQ ID NO: 21 is Gly, Ala, Val, Leu, Ile, Pro, Phe, Met, or Trp;

(d) the second polypeptide chain comprises amino acids 20-304 of SEQ ID NO: 22, wherein X at position 188 of SEQ ID NO: 22 is Ser or Cys; or (e) both (a) and (b); both (c) and (d); both (a) and (d); or both (b) and (c).

22. An isolated or purified nucleic acid comprising a nucleotide sequence encoding the TCR according to claim 1.

23. An isolated or purified recombinant expression vector comprising the nucleic acid according to claim 22.

24. The recombinant expression vector of claim 23, wherein the nucleotide sequence encoding the alpha chain is positioned 5' of the nucleotide sequence encoding the beta chain.

25. An isolated or purified T cell comprising the recombinant expression vector according to claim 23.

26. An isolated or purified population of cells comprising the T cell according to claim 25.

27. A pharmaceutical composition comprising (a) the TCR according to claim 1 and (b) a pharmaceutically acceptable carrier.

28. A method of detecting the presence of cancer in a human, the method comprising:

(a) contacting a sample comprising cells of the human with the TCR according to claim 1, thereby forming a complex comprising the cells of the human that are cancerous and the TCR; and (b) detecting the complex, wherein detection of the complex is indicative of the presence of cancer in the human, wherein the cells of the human that are cancerous express the mutated EGFR amino acid sequence of AIKTSP-KANKEIL (SEQ ID NO: 36) presented by an HLA Class II molecule that is a heterodimer of an HLA-DPA1*02:01 chain and an HLA-DPB1*01:01 chain.

29. A method of treating cancer in a human, comprising administering to the human $1\times10^6$ to $1\times10^{12}$ or more CD4$^+$ helper T cells comprising the recombinant expression vector according to claim 23, in an amount effective to treat cancer in the human, wherein the cancer expresses the mutated EGFR amino acid sequence of AIKTSPKANKEIL (SEQ ID NO: 36) presented by an HLA Class II molecule that is a heterodimer of an HLA-DPA1*02:01 chain and an HLA-DPB1*01:01 chain.

\* \* \* \* \*

SEQUENCE LISTING

<160> NUMBER OF SEQ ID NOS: 51

<210> SEQ ID NO 1
<211> LENGTH: 1210
<212> TYPE: PRT
<213> ORGANISM: Homo sapiens

<400> SEQUENCE: 1

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365
```

-continued

```
Leu His Ile Leu Pro Val Ala Phe Arg Gly Asp Ser Phe Thr His Thr
    370             375             380

Pro Pro Leu Asp Pro Gln Glu Leu Asp Ile Leu Lys Thr Val Lys Glu
385             390             395             400

Ile Thr Gly Phe Leu Leu Ile Gln Ala Trp Pro Glu Asn Arg Thr Asp
            405             410             415

Leu His Ala Phe Glu Asn Leu Glu Ile Ile Arg Gly Arg Thr Lys Gln
            420             425             430

His Gly Gln Phe Ser Leu Ala Val Val Ser Leu Asn Ile Thr Ser Leu
            435             440             445

Gly Leu Arg Ser Leu Lys Glu Ile Ser Asp Gly Asp Val Ile Ile Ser
    450             455             460

Gly Asn Lys Asn Leu Cys Tyr Ala Asn Thr Ile Asn Trp Lys Lys Leu
465             470             475             480

Phe Gly Thr Ser Gly Gln Lys Thr Lys Ile Ile Ser Asn Arg Gly Glu
            485             490             495

Asn Ser Cys Lys Ala Thr Gly Gln Val Cys His Ala Leu Cys Ser Pro
            500             505             510

Glu Gly Cys Trp Gly Pro Glu Pro Arg Asp Cys Val Ser Cys Arg Asn
            515             520             525

Val Ser Arg Gly Arg Glu Cys Val Asp Lys Cys Asn Leu Leu Glu Gly
    530             535             540

Glu Pro Arg Glu Phe Val Glu Asn Ser Glu Cys Ile Gln Cys His Pro
545             550             555             560

Glu Cys Leu Pro Gln Ala Met Asn Ile Thr Cys Thr Gly Arg Gly Pro
            565             570             575

Asp Asn Cys Ile Gln Cys Ala His Tyr Ile Asp Gly Pro His Cys Val
            580             585             590

Lys Thr Cys Pro Ala Gly Val Met Gly Glu Asn Asn Thr Leu Val Trp
            595             600             605

Lys Tyr Ala Asp Ala Gly His Val Cys His Leu Cys His Pro Asn Cys
    610             615             620

Thr Tyr Gly Cys Thr Gly Pro Gly Leu Glu Gly Cys Pro Thr Asn Gly
625             630             635             640

Pro Lys Ile Pro Ser Ile Ala Thr Gly Met Val Gly Ala Leu Leu Leu
            645             650             655

Leu Leu Val Val Ala Leu Gly Ile Gly Leu Phe Met Arg Arg Arg His
            660             665             670

Ile Val Arg Lys Arg Thr Leu Arg Arg Leu Leu Gln Glu Arg Glu Leu
            675             680             685

Val Glu Pro Leu Thr Pro Ser Gly Glu Ala Pro Asn Gln Ala Leu Leu
    690             695             700

Arg Ile Leu Lys Glu Thr Glu Phe Lys Lys Ile Lys Val Leu Gly Ser
705             710             715             720

Gly Ala Phe Gly Thr Val Tyr Lys Gly Leu Trp Ile Pro Glu Gly Glu
            725             730             735

Lys Val Lys Ile Pro Val Ala Ile Lys Glu Leu Arg Glu Ala Thr Ser
            740             745             750

Pro Lys Ala Asn Lys Glu Ile Leu Asp Glu Ala Tyr Val Met Ala Ser
            755             760             765

Val Asp Asn Pro His Val Cys Arg Leu Leu Gly Ile Cys Leu Thr Ser
    770             775             780

Thr Val Gln Leu Ile Thr Gln Leu Met Pro Phe Gly Cys Leu Leu Asp
```

-continued

```
785                    790                   795                    800

Tyr Val Arg Glu His Lys Asp Asn Ile Gly Ser Gln Tyr Leu Leu Asn
                805                   810                   815

Trp Cys Val Gln Ile Ala Lys Gly Met Asn Tyr Leu Glu Asp Arg Arg
                820                   825                   830

Leu Val His Arg Asp Leu Ala Ala Arg Asn Val Leu Val Lys Thr Pro
            835                   840                   845

Gln His Val Lys Ile Thr Asp Phe Gly Leu Ala Lys Leu Leu Gly Ala
    850                   855                   860

Glu Glu Lys Glu Tyr His Ala Glu Gly Gly Lys Val Pro Ile Lys Trp
865                   870                   875                   880

Met Ala Leu Glu Ser Ile Leu His Arg Ile Tyr Thr His Gln Ser Asp
                885                   890                   895

Val Trp Ser Tyr Gly Val Thr Val Trp Glu Leu Met Thr Phe Gly Ser
                900                   905                   910

Lys Pro Tyr Asp Gly Ile Pro Ala Ser Glu Ile Ser Ser Ile Leu Glu
                915                   920                   925

Lys Gly Glu Arg Leu Pro Gln Pro Pro Ile Cys Thr Ile Asp Val Tyr
    930                   935                   940

Met Ile Met Val Lys Cys Trp Met Ile Asp Ala Asp Ser Arg Pro Lys
945                   950                   955                   960

Phe Arg Glu Leu Ile Ile Glu Phe Ser Lys Met Ala Arg Asp Pro Gln
                965                   970                   975

Arg Tyr Leu Val Ile Gln Gly Asp Glu Arg Met His Leu Pro Ser Pro
                980                   985                   990

Thr Asp Ser Asn Phe Tyr Arg Ala Leu Met Asp Glu Glu Asp Met Asp
                995                   1000                  1005

Asp Val Val Asp Ala Asp Glu Tyr Leu Ile Pro Gln Gln Gly Phe
    1010                  1015                  1020

Phe Ser Ser Pro Ser Thr Ser Arg Thr Pro Leu Leu Ser Ser Leu
    1025                  1030                  1035

Ser Ala Thr Ser Asn Asn Ser Thr Val Ala Cys Ile Asp Arg Asn
    1040                  1045                  1050

Gly Leu Gln Ser Cys Pro Ile Lys Glu Asp Ser Phe Leu Gln Arg
    1055                  1060                  1065

Tyr Ser Ser Asp Pro Thr Gly Ala Leu Thr Glu Asp Ser Ile Asp
    1070                  1075                  1080

Asp Thr Phe Leu Pro Val Pro Glu Tyr Ile Asn Gln Ser Val Pro
    1085                  1090                  1095

Lys Arg Pro Ala Gly Ser Val Gln Asn Pro Val Tyr His Asn Gln
    1100                  1105                  1110

Pro Leu Asn Pro Ala Pro Ser Arg Asp Pro His Tyr Gln Asp Pro
    1115                  1120                  1125

His Ser Thr Ala Val Gly Asn Pro Glu Tyr Leu Asn Thr Val Gln
    1130                  1135                  1140

Pro Thr Cys Val Asn Ser Thr Phe Asp Ser Pro Ala His Trp Ala
    1145                  1150                  1155

Gln Lys Gly Ser His Gln Ile Ser Leu Asp Asn Pro Asp Tyr Gln
    1160                  1165                  1170

Gln Asp Phe Phe Pro Lys Glu Ala Lys Pro Asn Gly Ile Phe Lys
    1175                  1180                  1185

Gly Ser Thr Ala Glu Asn Ala Glu Tyr Leu Arg Val Ala Pro Gln
    1190                  1195                  1200
```

-continued

```
Ser Ser   Glu Phe Ile Gly Ala
    1205                  1210

<210> SEQ ID NO 2
<211> LENGTH: 1205
<212> TYPE: PRT
<213> ORGANISM: Homo sapiens

<400> SEQUENCE: 2

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
```

-continued

```
                355                   360                   365

Leu His Ile Leu Pro Val Ala Phe Arg Gly Asp Ser Phe Thr His Thr
    370                   375                   380

Pro Pro Leu Asp Pro Gln Glu Leu Asp Ile Leu Lys Thr Val Lys Glu
385                   390                   395                   400

Ile Thr Gly Phe Leu Leu Ile Gln Ala Trp Pro Glu Asn Arg Thr Asp
                405                   410                   415

Leu His Ala Phe Glu Asn Leu Glu Ile Ile Arg Gly Arg Thr Lys Gln
                420                   425                   430

His Gly Gln Phe Ser Leu Ala Val Val Ser Leu Asn Ile Thr Ser Leu
                435                   440                   445

Gly Leu Arg Ser Leu Lys Glu Ile Ser Asp Gly Asp Val Ile Ile Ser
    450                   455                   460

Gly Asn Lys Asn Leu Cys Tyr Ala Asn Thr Ile Asn Trp Lys Lys Leu
465                   470                   475                   480

Phe Gly Thr Ser Gly Gln Lys Thr Lys Ile Ile Ser Asn Arg Gly Glu
                485                   490                   495

Asn Ser Cys Lys Ala Thr Gly Gln Val Cys His Ala Leu Cys Ser Pro
                500                   505                   510

Glu Gly Cys Trp Gly Pro Glu Pro Arg Asp Cys Val Ser Cys Arg Asn
                515                   520                   525

Val Ser Arg Gly Arg Glu Cys Val Asp Lys Cys Asn Leu Leu Glu Gly
    530                   535                   540

Glu Pro Arg Glu Phe Val Glu Asn Ser Glu Cys Ile Gln Cys His Pro
545                   550                   555                   560

Glu Cys Leu Pro Gln Ala Met Asn Ile Thr Cys Thr Gly Arg Gly Pro
                565                   570                   575

Asp Asn Cys Ile Gln Cys Ala His Tyr Ile Asp Gly Pro His Cys Val
                580                   585                   590

Lys Thr Cys Pro Ala Gly Val Met Gly Glu Asn Asn Thr Leu Val Trp
                595                   600                   605

Lys Tyr Ala Asp Ala Gly His Val Cys His Leu Cys His Pro Asn Cys
    610                   615                   620

Thr Tyr Gly Cys Thr Gly Pro Gly Leu Glu Gly Cys Pro Thr Asn Gly
625                   630                   635                   640

Pro Lys Ile Pro Ser Ile Ala Thr Gly Met Val Gly Ala Leu Leu Leu
                645                   650                   655

Leu Leu Val Val Ala Leu Gly Ile Gly Leu Phe Met Arg Arg Arg His
                660                   665                   670

Ile Val Arg Lys Arg Thr Leu Arg Arg Leu Leu Gln Glu Arg Glu Leu
                675                   680                   685

Val Glu Pro Leu Thr Pro Ser Gly Glu Ala Pro Asn Gln Ala Leu Leu
                690                   695                   700

Arg Ile Leu Lys Glu Thr Glu Phe Lys Lys Ile Lys Val Leu Gly Ser
705                   710                   715                   720

Gly Ala Phe Gly Thr Val Tyr Lys Gly Leu Trp Ile Pro Glu Gly Glu
                725                   730                   735

Lys Val Lys Ile Pro Val Ala Ile Lys Thr Ser Pro Lys Ala Asn Lys
                740                   745                   750

Glu Ile Leu Asp Glu Ala Tyr Val Met Ala Ser Val Asp Asn Pro His
                755                   760                   765

Val Cys Arg Leu Leu Gly Ile Cys Leu Thr Ser Thr Val Gln Leu Ile
    770                   775                   780
```

-continued

```
Thr Gln Leu Met Pro Phe Gly Cys Leu Leu Asp Tyr Val Arg Glu His
785                 790                 795                 800

Lys Asp Asn Ile Gly Ser Gln Tyr Leu Leu Asn Trp Cys Val Gln Ile
                805                 810                 815

Ala Lys Gly Met Asn Tyr Leu Glu Asp Arg Arg Leu Val His Arg Asp
            820                 825                 830

Leu Ala Ala Arg Asn Val Leu Val Lys Thr Pro Gln His Val Lys Ile
        835                 840                 845

Thr Asp Phe Gly Leu Ala Lys Leu Leu Gly Ala Glu Glu Lys Glu Tyr
    850                 855                 860

His Ala Glu Gly Gly Lys Val Pro Ile Lys Trp Met Ala Leu Glu Ser
865                 870                 875                 880

Ile Leu His Arg Ile Tyr Thr His Gln Ser Asp Val Trp Ser Tyr Gly
                885                 890                 895

Val Thr Val Trp Glu Leu Met Thr Phe Gly Ser Lys Pro Tyr Asp Gly
                900                 905                 910

Ile Pro Ala Ser Glu Ile Ser Ser Ile Leu Glu Lys Gly Glu Arg Leu
            915                 920                 925

Pro Gln Pro Pro Ile Cys Thr Ile Asp Val Tyr Met Ile Met Val Lys
        930                 935                 940

Cys Trp Met Ile Asp Ala Asp Ser Arg Pro Lys Phe Arg Glu Leu Ile
945                 950                 955                 960

Ile Glu Phe Ser Lys Met Ala Arg Asp Pro Gln Arg Tyr Leu Val Ile
                965                 970                 975

Gln Gly Asp Glu Arg Met His Leu Pro Ser Pro Thr Asp Ser Asn Phe
            980                 985                 990

Tyr Arg Ala Leu Met Asp Glu Glu  Asp Met Asp Asp Val  Val Asp Ala
    995                 1000                1005

Asp Glu  Tyr Leu Ile Pro Gln  Gln Gly Phe Phe Ser  Ser Pro Ser
    1010                1015                1020

Thr Ser  Arg Thr Pro Leu Leu  Ser Ser Leu Ser Ala  Thr Ser Asn
    1025                1030                1035

Asn Ser  Thr Val Ala Cys Ile  Asp Arg Asn Gly Leu  Gln Ser Cys
    1040                1045                1050

Pro Ile  Lys Glu Asp Ser Phe  Leu Gln Arg Tyr Ser  Ser Asp Pro
    1055                1060                1065

Thr Gly  Ala Leu Thr Glu Asp  Ser Ile Asp Asp Thr  Phe Leu Pro
    1070                1075                1080

Val Pro  Glu Tyr Ile Asn Gln  Ser Val Pro Lys Arg  Pro Ala Gly
    1085                1090                1095

Ser Val  Gln Asn Pro Val Tyr  His Asn Gln Pro Leu  Asn Pro Ala
    1100                1105                1110

Pro Ser  Arg Asp Pro His Tyr  Gln Asp Pro His Ser  Thr Ala Val
    1115                1120                1125

Gly Asn  Pro Glu Tyr Leu Asn  Thr Val Gln Pro Thr  Cys Val Asn
    1130                1135                1140

Ser Thr  Phe Asp Ser Pro Ala  His Trp Ala Gln Lys  Gly Ser His
    1145                1150                1155

Gln Ile  Ser Leu Asp Asn Pro  Asp Tyr Gln Gln Asp  Phe Phe Pro
    1160                1165                1170

Lys Glu  Ala Lys Pro Asn Gly  Ile Phe Lys Gly Ser  Thr Ala Glu
    1175                1180                1185
```

```
Asn Ala  Glu Tyr Leu Arg Val  Ala Pro Gln Ser Ser  Glu Phe Ile
    1190             1195            1200

Gly Ala
    1205
```

<210> SEQ ID NO 3
<211> LENGTH: 6
<212> TYPE: PRT
<213> ORGANISM: Homo sapiens

<400> SEQUENCE: 3

```
Ser Ser Val Pro Pro Tyr
1               5
```

<210> SEQ ID NO 4
<211> LENGTH: 8
<212> TYPE: PRT
<213> ORGANISM: Homo sapiens

<400> SEQUENCE: 4

```
Tyr Thr Ser Ala Ala Thr Leu Val
1               5
```

<210> SEQ ID NO 5
<211> LENGTH: 13
<212> TYPE: PRT
<213> ORGANISM: Homo sapiens

<400> SEQUENCE: 5

```
Cys Ala Val Ser Glu Asp Ser Asn Tyr Gln Leu Ile Trp
1               5                   10
```

<210> SEQ ID NO 6
<211> LENGTH: 6
<212> TYPE: PRT
<213> ORGANISM: Homo sapiens

<400> SEQUENCE: 6

```
Gly Thr Ser Asn Pro Asn
1               5
```

<210> SEQ ID NO 7
<211> LENGTH: 5
<212> TYPE: PRT
<213> ORGANISM: Homo sapiens

<400> SEQUENCE: 7

```
Ser Val Gly Ile Gly
1               5
```

<210> SEQ ID NO 8
<211> LENGTH: 14
<212> TYPE: PRT
<213> ORGANISM: Homo sapiens

<400> SEQUENCE: 8

```
Cys Ala Tyr Ser Pro Gly Leu Ala Ser Asp Thr Gln Tyr Phe
1               5                   10
```

<210> SEQ ID NO 9
<211> LENGTH: 132
<212> TYPE: PRT
<213> ORGANISM: Homo sapiens

<400> SEQUENCE: 9

```
Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
            20                  25                  30

Ser Glu Gly Ala Leu Val Leu Leu Arg Cys Asn Tyr Ser Ser Ser Val
        35                  40                  45

Pro Pro Tyr Leu Phe Trp Tyr Val Gln Tyr Pro Asn Gln Gly Leu Gln
    50                  55                  60

Leu Leu Leu Lys Tyr Thr Ser Ala Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
            100                 105                 110

Ser Glu Asp Ser Asn Tyr Gln Leu Ile Trp Gly Ala Gly Thr Lys Leu
        115                 120                 125

Ile Ile Lys Pro
    130

<210> SEQ ID NO 10
<211> LENGTH: 130
<212> TYPE: PRT
<213> ORGANISM: Homo sapiens

<400> SEQUENCE: 10

Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
            20                  25                  30

Gly Ser Pro Leu Ser Leu Glu Cys Thr Val Glu Gly Thr Ser Asn Pro
        35                  40                  45

Asn Leu Tyr Trp Tyr Arg Gln Ala Ala Gly Arg Gly Leu Gln Leu Leu
    50                  55                  60

Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Tyr Ser Pro
            100                 105                 110

Gly Leu Ala Ser Asp Thr Gln Tyr Phe Gly Pro Gly Thr Arg Leu Thr
        115                 120                 125

Val Leu
    130

<210> SEQ ID NO 11
<211> LENGTH: 133
<212> TYPE: PRT
<213> ORGANISM: Artificial Sequence
<220> FEATURE:
<223> OTHER INFORMATION: Synthetic

<400> SEQUENCE: 11

Met Ala Leu Leu Leu Leu Val Pro Val Leu Glu Val Ile Phe Thr Leu
1               5                   10                  15

Gly Gly Thr Arg Ala Gln Ser Val Thr Gln Leu Gly Ser His Val Ser
            20                  25                  30
```

-continued

```
Val Ser Glu Gly Ala Leu Val Leu Leu Arg Cys Asn Tyr Ser Ser Ser
        35                  40                  45

Val Pro Pro Tyr Leu Phe Trp Tyr Val Gln Tyr Pro Asn Gln Gly Leu
    50                  55                  60

Gln Leu Leu Leu Lys Tyr Thr Ser Ala Ala Thr Leu Val Lys Gly Ile
65                  70                  75                  80

Asn Gly Phe Glu Ala Glu Phe Lys Lys Ser Glu Thr Ser Phe His Leu
                85                  90                  95

Thr Lys Pro Ser Ala His Met Ser Asp Ala Ala Glu Tyr Phe Cys Ala
                100                 105                 110

Val Ser Glu Asp Ser Asn Tyr Gln Leu Ile Trp Gly Ala Gly Thr Lys
        115                 120                 125

Leu Ile Ile Lys Pro
    130
```

```
<210> SEQ ID NO 12
<211> LENGTH: 131
<212> TYPE: PRT
<213> ORGANISM: Artificial Sequence
<220> FEATURE:
<223> OTHER INFORMATION: Synthetic

<400> SEQUENCE: 12
```

```
Met Ala Leu Cys Ser Leu Leu Ala Leu Leu Leu Gly Thr Phe Phe Gly
1               5                   10                  15

Val Arg Ser Gln Thr Ile His Gln Trp Pro Ala Thr Leu Val Gln Pro
                20                  25                  30

Val Gly Ser Pro Leu Ser Leu Glu Cys Thr Val Glu Gly Thr Ser Asn
        35                  40                  45

Pro Asn Leu Tyr Trp Tyr Arg Gln Ala Ala Gly Arg Gly Leu Gln Leu
    50                  55                  60

Leu Phe Tyr Ser Val Gly Ile Gly Gln Ile Ser Ser Glu Val Pro Gln
65                  70                  75                  80

Asn Leu Ser Ala Ser Arg Pro Gln Asp Arg Gln Phe Ile Leu Ser Ser
                85                  90                  95

Lys Lys Leu Leu Leu Ser Asp Ser Gly Phe Tyr Leu Cys Ala Tyr Ser
                100                 105                 110

Pro Gly Leu Ala Ser Asp Thr Gln Tyr Phe Gly Pro Gly Thr Arg Leu
        115                 120                 125

Thr Val Leu
    130
```

```
<210> SEQ ID NO 13
<211> LENGTH: 141
<212> TYPE: PRT
<213> ORGANISM: Homo sapiens

<400> SEQUENCE: 13
```

```
Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
```

-continued

```
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
        130                 135                 140
```

<210> SEQ ID NO 14
<211> LENGTH: 179
<212> TYPE: PRT
<213> ORGANISM: Homo sapiens

<400> SEQUENCE: 14

```
Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly
```

<210> SEQ ID NO 15
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (48)..(48)
<223> OTHER INFORMATION: X is Thr or Cys
<220> FEATURE:
<221> NAME/KEY: MISC_FEATURE
<222> LOCATION: (112)..(112)
<223> OTHER INFORMATION: X is Ser, Ala, Val, Leu, Ile, Pro, Phe, Met, or
        Trp
<220> FEATURE:
<221> NAME/KEY: MISC_FEATURE
<222> LOCATION: (114)..(114)
<223> OTHER INFORMATION: X is Met, Ala, Val, Leu, Ile, Pro, Phe, or Trp
<220> FEATURE:
<221> NAME/KEY: MISC_FEATURE
```

```
<222> LOCATION: (115)..(115)
<223> OTHER INFORMATION: X is Gly, Ala, Val, Leu, Ile, Pro, Phe, Met, or
      Trp

<400> SEQUENCE: 15

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
                20                  25                  30

Asn Val Pro Lys Thr Met Glu Ser Gly Thr Phe Ile Thr Asp Lys Xaa
            35                  40                  45

Val Leu Asp Met Lys Ala Met Asp Ser Lys Ser Asn Gly Ala Ile Ala
        50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Xaa
                100                 105                 110

Val Xaa Xaa Leu Arg Ile Leu Leu Leu Lys Val Ala Gly Phe Asn Leu
        115                 120                 125

Leu Met Thr Leu Arg Leu Trp Ser Ser
        130                 135

<210> SEQ ID NO 16
<211> LENGTH: 173
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (57)..(57)
<223> OTHER INFORMATION: X is Ser or Cys

<400> SEQUENCE: 16

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
                20                  25                  30

Ala Arg Gly Phe Phe Pro Asp His Val Glu Leu Ser Trp Trp Val Asn
            35                  40                  45

Gly Lys Glu Val His Ser Gly Val Xaa Thr Asp Pro Gln Ala Tyr Lys
        50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
                100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
        130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

```
<210> SEQ ID NO 17
<211> LENGTH: 137
<212> TYPE: PRT
<213> ORGANISM: Mus musculus

<400> SEQUENCE: 17

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
            115                 120                 125

Leu Met Thr Leu Arg Leu Trp Ser Ser
        130                 135

<210> SEQ ID NO 18
<211> LENGTH: 173
<212> TYPE: PRT
<213> ORGANISM: Mus musculus

<400> SEQUENCE: 18

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
            115                 120                 125

Ile Thr Ser Ala Ser Tyr Gln Gln Gly Val Leu Ser Ala Thr Ile Leu
        130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 19
```

-continued

```
<211> LENGTH: 273
<212> TYPE: PRT
<213> ORGANISM: Homo sapiens

<400> SEQUENCE: 19

Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
            20                  25                  30

Ser Glu Gly Ala Leu Val Leu Leu Arg Cys Asn Tyr Ser Ser Ser Val
            35                  40                  45

Pro Pro Tyr Leu Phe Trp Tyr Val Gln Tyr Pro Asn Gln Gly Leu Gln
        50                  55                  60

Leu Leu Leu Lys Tyr Thr Ser Ala Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
            100                 105                 110

Ser Glu Asp Ser Asn Tyr Gln Leu Ile Trp Gly Ala Gly Thr Lys Leu
            115                 120                 125

Ile Ile Lys Pro Asp Ile Gln Asn Pro Asp Pro Ala Val Tyr Gln Leu
        130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
                180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
        210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 20
<211> LENGTH: 309
<212> TYPE: PRT
<213> ORGANISM: Homo sapiens

<400> SEQUENCE: 20

Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
            20                  25                  30

Gly Ser Pro Leu Ser Leu Glu Cys Thr Val Glu Gly Thr Ser Asn Pro
            35                  40                  45

Asn Leu Tyr Trp Tyr Arg Gln Ala Ala Gly Arg Gly Leu Gln Leu Leu
        50                  55                  60
```

```
Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Tyr Ser Pro
                100                 105                 110

Gly Leu Ala Ser Asp Thr Gln Tyr Phe Gly Pro Gly Thr Arg Leu Thr
        115                 120                 125

Val Leu Glu Asp Leu Lys Asn Val Phe Pro Pro Glu Val Ala Val Phe
        130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
                180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
                260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
        290                 295                 300

Lys Asp Ser Arg Gly
305
```

```
<210> SEQ ID NO 21
<211> LENGTH: 270
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (181)..(181)
<223> OTHER INFORMATION: X is Thr or Cys
<220> FEATURE:
<221> NAME/KEY: MISC_FEATURE
<222> LOCATION: (245)..(245)
<223> OTHER INFORMATION: X is Ser, Ala, Val, Leu, Ile, Pro, Phe, Met, or
     Trp
<220> FEATURE:
<221> NAME/KEY: MISC_FEATURE
<222> LOCATION: (247)..(247)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (248)..(248)
<223> OTHER INFORMATION: X is Gly, Ala, Val, Leu, Ile, Pro, Phe, Met, or
     Trp

<400> SEQUENCE: 21

Met Ala Leu Leu Leu Leu Val Pro Val Leu Glu Val Ile Phe Thr Leu
1               5                   10                  15
```

-continued

```
Gly Gly Thr Arg Ala Gln Ser Val Thr Gln Leu Gly Ser His Val Ser
        20              25              30

Val Ser Glu Gly Ala Leu Val Leu Leu Arg Cys Asn Tyr Ser Ser Ser
        35              40              45

Val Pro Pro Tyr Leu Phe Trp Tyr Val Gln Tyr Pro Asn Gln Gly Leu
    50              55              60

Gln Leu Leu Leu Lys Tyr Thr Ser Ala Ala Thr Leu Val Lys Gly Ile
65              70              75              80

Asn Gly Phe Glu Ala Glu Phe Lys Lys Ser Glu Thr Ser Phe His Leu
            85              90              95

Thr Lys Pro Ser Ala His Met Ser Asp Ala Ala Glu Tyr Phe Cys Ala
            100             105             110

Val Ser Glu Asp Ser Asn Tyr Gln Leu Ile Trp Gly Ala Gly Thr Lys
        115             120             125

Leu Ile Ile Lys Pro Asp Ile Gln Asn Pro Glu Pro Ala Val Tyr Gln
    130             135             140

Leu Lys Asp Pro Arg Ser Gln Asp Ser Thr Leu Cys Leu Phe Thr Asp
145             150             155             160

Phe Asp Ser Gln Ile Asn Val Pro Lys Thr Met Glu Ser Gly Thr Phe
            165             170             175

Ile Thr Asp Lys Xaa Val Leu Asp Met Lys Ala Met Asp Ser Lys Ser
            180             185             190

Asn Gly Ala Ile Ala Trp Ser Asn Gln Thr Ser Phe Thr Cys Gln Asp
            195             200             205

Ile Phe Lys Glu Thr Asn Ala Thr Tyr Pro Ser Ser Asp Val Pro Cys
    210             215             220

Asp Ala Thr Leu Thr Glu Lys Ser Phe Glu Thr Asp Met Asn Leu Asn
225             230             235             240

Phe Gln Asn Leu Xaa Val Xaa Xaa Leu Arg Ile Leu Leu Leu Lys Val
            245             250             255

Ala Gly Phe Asn Leu Leu Met Thr Leu Arg Leu Trp Ser Ser
            260             265             270

<210> SEQ ID NO 22
<211> LENGTH: 304
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (188)..(188)
<223> OTHER INFORMATION: X is Ser or Cys

<400> SEQUENCE: 22

Met Ala Leu Cys Ser Leu Leu Ala Leu Leu Leu Gly Thr Phe Phe Gly
1               5               10              15

Val Arg Ser Gln Thr Ile His Gln Trp Pro Ala Thr Leu Val Gln Pro
            20              25              30

Val Gly Ser Pro Leu Ser Leu Glu Cys Thr Val Glu Gly Thr Ser Asn
        35              40              45

Pro Asn Leu Tyr Trp Tyr Arg Gln Ala Ala Gly Arg Gly Leu Gln Leu
    50              55              60

Leu Phe Tyr Ser Val Gly Ile Gly Gln Ile Ser Ser Glu Val Pro Gln
65              70              75              80

Asn Leu Ser Ala Ser Arg Pro Gln Asp Arg Gln Phe Ile Leu Ser Ser
            85              90              95
```

```
Lys Lys Leu Leu Leu Ser Asp Ser Gly Phe Tyr Leu Cys Ala Tyr Ser
            100                 105                 110

Pro Gly Leu Ala Ser Asp Thr Gln Tyr Phe Gly Pro Gly Thr Arg Leu
            115                 120                 125

Thr Val Leu Glu Asp Leu Arg Asn Val Thr Pro Pro Lys Val Ser Leu
            130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Xaa Thr Asp Pro Gln
            180                 185                 190

Ala Tyr Lys Glu Ser Asn Tyr Ser Tyr Cys Leu Ser Ser Arg Leu Arg
            195                 200                 205

Val Ser Ala Thr Phe Trp His Asn Pro Arg Asn His Phe Arg Cys Gln
            210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
                260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
            290                 295                 300
```

```
<210> SEQ ID NO 23
<211> LENGTH: 270
<212> TYPE: PRT
<213> ORGANISM: Artificial Sequence
<220> FEATURE:
<223> OTHER INFORMATION: Synthetic

<400> SEQUENCE: 23
```

```
Met Ala Leu Leu Leu Leu Val Pro Val Leu Glu Val Ile Phe Thr Leu
1                   5                   10                  15

Gly Gly Thr Arg Ala Gln Ser Val Thr Gln Leu Gly Ser His Val Ser
            20                  25                  30

Val Ser Glu Gly Ala Leu Val Leu Leu Arg Cys Asn Tyr Ser Ser Ser
            35                  40                  45

Val Pro Pro Tyr Leu Phe Trp Tyr Val Gln Tyr Pro Asn Gln Gly Leu
            50                  55                  60

Gln Leu Leu Leu Lys Tyr Thr Ser Ala Ala Thr Leu Val Lys Gly Ile
65                  70                  75                  80

Asn Gly Phe Glu Ala Glu Phe Lys Lys Ser Glu Thr Ser Phe His Leu
                85                  90                  95

Thr Lys Pro Ser Ala His Met Ser Asp Ala Ala Glu Tyr Phe Cys Ala
            100                 105                 110

Val Ser Glu Asp Ser Asn Tyr Gln Leu Ile Trp Gly Ala Gly Thr Lys
            115                 120                 125

Leu Ile Ile Lys Pro Asp Ile Gln Asn Pro Glu Pro Ala Val Tyr Gln
            130                 135                 140

Leu Lys Asp Pro Arg Ser Gln Asp Ser Thr Leu Cys Leu Phe Thr Asp
145                 150                 155                 160
```

-continued

```
Phe Asp Ser Gln Ile Asn Val Pro Lys Thr Met Glu Ser Gly Thr Phe
                165                 170                 175

Ile Thr Asp Lys Cys Val Leu Asp Met Lys Ala Met Asp Ser Lys Ser
                180                 185                 190

Asn Gly Ala Ile Ala Trp Ser Asn Gln Thr Ser Phe Thr Cys Gln Asp
                195                 200                 205

Ile Phe Lys Glu Thr Asn Ala Thr Tyr Pro Ser Ser Asp Val Pro Cys
            210                 215                 220

Asp Ala Thr Leu Thr Glu Lys Ser Phe Glu Thr Asp Met Asn Leu Asn
225                 230                 235                 240

Phe Gln Asn Leu Leu Val Ile Val Leu Arg Ile Leu Leu Leu Lys Val
                245                 250                 255

Ala Gly Phe Asn Leu Leu Met Thr Leu Arg Leu Trp Ser Ser
                260                 265                 270

<210> SEQ ID NO 24
<211> LENGTH: 304
<212> TYPE: PRT
<213> ORGANISM: Artificial Sequence
<220> FEATURE:
<223> OTHER INFORMATION: Synthetic

<400> SEQUENCE: 24

Met Ala Leu Cys Ser Leu Leu Ala Leu Leu Leu Gly Thr Phe Phe Gly
1               5                   10                  15

Val Arg Ser Gln Thr Ile His Gln Trp Pro Ala Thr Leu Val Gln Pro
                20                  25                  30

Val Gly Ser Pro Leu Ser Leu Glu Cys Thr Val Glu Gly Thr Ser Asn
                35                  40                  45

Pro Asn Leu Tyr Trp Tyr Arg Gln Ala Ala Gly Arg Gly Leu Gln Leu
            50                  55                  60

Leu Phe Tyr Ser Val Gly Ile Gly Gln Ile Ser Ser Glu Val Pro Gln
65                  70                  75                  80

Asn Leu Ser Ala Ser Arg Pro Gln Asp Arg Gln Phe Ile Leu Ser Ser
                85                  90                  95

Lys Lys Leu Leu Leu Ser Asp Ser Gly Phe Tyr Leu Cys Ala Tyr Ser
                100                 105                 110

Pro Gly Leu Ala Ser Asp Thr Gln Tyr Phe Gly Pro Gly Thr Arg Leu
            115                 120                 125

Thr Val Leu Glu Asp Leu Arg Asn Val Thr Pro Pro Lys Val Ser Leu
            130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
                180                 185                 190

Ala Tyr Lys Glu Ser Asn Tyr Ser Tyr Cys Leu Ser Ser Arg Leu Arg
                195                 200                 205

Val Ser Ala Thr Phe Trp His Asn Pro Arg Asn His Phe Arg Cys Gln
            210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255
```

```
Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300

<210> SEQ ID NO 25
<211> LENGTH: 19
<212> TYPE: PRT
<213> ORGANISM: Artificial Sequence
<220> FEATURE:
<223> OTHER INFORMATION: Synthetic

<400> SEQUENCE: 25

Ala Thr Asn Phe Ser Leu Leu Lys Gln Ala Gly Asp Val Glu Glu Asn
1               5                   10                  15

Pro Gly Pro

<210> SEQ ID NO 26
<211> LENGTH: 822
<212> TYPE: DNA
<213> ORGANISM: Homo sapiens

<400> SEQUENCE: 26
atgctcctgc tgctcgtccc agtgctcgag gtgattttta ccctgggagg aaccagagcc      60
cagtcggtga cccagcttgg cagccacgtc tctgtctctg agggagccct ggttctgctg     120
aggtgcaact actcatcgtc tgttccacca tatctcttct ggtatgtgca ataccccaac     180
caaggactcc agcttctcct gaagtacaca tcagcggcca ccctggttaa aggcatcaac     240
ggttttgagg ctgaatttaa aagagtgaa acctccttcc acctgacgaa accctcagcc      300
catatgagcg acgcggctga gtacttctgt gctgtgagtg aggatagcaa ctatcagtta     360
atctggggcg ctgggaccaa gctaattata aagccagata tccagaaccc tgaccctgcc     420
gtgtaccagc tgagagactc taaatccagt gacaagtctg tctgcctatt caccgatttt     480
gattctcaaa caaatgtgtc acaaagtaag gattctgatg tgtatatcac agacaaaaact    540 gtgctagaca tgaggtctat ggacttcaag agcaacagtg ctgtggcctg gagcaacaaa     600
tctgactttg catgtgcaaa cgccttcaac aacagcatta ttccagaaga caccttcttc     660
cccagcccag aaagttcctg tgatgtcaag ctggtcgaga aaagctttga aacagatacg     720
aacctaaact ttcaaaacct gtcagtgatt gggttccgaa tcctcctcct gaaagtggcc     780
gggtttaatc tgctcatgac gctgcggctg tggtccagct ga                        822

<210> SEQ ID NO 27
<211> LENGTH: 930
<212> TYPE: DNA
<213> ORGANISM: Homo sapiens

<400> SEQUENCE: 27
atgctctgct ctctccttgc ccttctcctg ggcactttct ttgggggtcag atctcagact     60 attcatcaat ggccagcgac cctggtgcag cctgtgggca gccgctctc tctggagtgc       120 actgtggagg aacatcaaa ccccaaccta tactggtacc gacaggctgc aggcagggc        180 ctccagctgc tcttctactc cgttggtatt ggccagatca gctctgaggt gccccagaat     240
ctctcagcct ccagacccca ggaccggcag ttcatcctga gttctaagaa gctcctcctc     300
```

```
agtgactctg gcttctatct ctgtgcctac tcaccgggac tagcgtcaga tacgcagtat      360
tttggcccag gcacccggct gacagtgctc gaggacctga aaaacgtgtt cccacccgag      420
gtcgctgtgt ttgagccatc agaagcagag atctcccaca cccaaaaggc cacactggtg      480
tgcctggcca caggcttcta ccccgaccac gtggagctga gctggtgggt gaatgggaag      540
gaggtgcaca gtggggtcag cacagacccg cagcccctca aggagcagcc cgccctcaat      600
gactccagat actgcctgag cagccgcctg agggtctcgg ccaccttctg gcagaacccc      660
cgcaaccact tccgctgtca agtccagttc tacgggctct cggagaatga cgagtggacc      720 caggatagg ccaaacccgt cacccagatc gtcagcgccg aggcctgggg tagagcagac      780
tgtggcttca cctccgagtc ttaccagcaa ggggtcctgt ctgccaccat cctctatgag      840
atcttgctag ggaaggccac cttgtatgcc gtgctggtca gtgccctcgt gctgatggcc      900
atggtcaaga gaaaggattc cagaggctag                                        930

<210> SEQ ID NO 28
<211> LENGTH: 810
<212> TYPE: DNA
<213> ORGANISM: Artificial Sequence
<220> FEATURE:
<223> OTHER INFORMATION: Synthetic

<400> SEQUENCE: 28
atggccctgc tgctgctggt gcccgtgctg gaagtgatct tcaccctggg aggaacaagg       60
gcacagtccg tgacacagct gggatctcac gtgagcgtgt ccgagggcgc cctggtgctg      120
ctgcgctgca actacagctc ctctgtgcca ccctatctgt tctggtacgt gcagtatccc      180
aatcagggcc tgcagctgct gctgaagtac acctccgccg ccacactggt gaagggcatc      240
aacggcttcg aggccgagtt taagaagtct gagaccagct tccacctgac aaagccttct      300
gcccacatga gcgatgccgc cgagtacttt tgtgccgtgt ccgaggactc taactatcag      360
ctgatctggg gcgccggcac caagctgatc atcaagcccg acatccagaa tccagagccc      420
gccgtgtatc agctgaagga ccctcggagc caggattcca ccctgtgcct gttcacagac      480
tttgattctc agatcaacgt gcccaagaca atggagagcg gcaccttcat cacagacaag      540
tgcgtgctgg atatgaaggc tatggactct aagagcaacg gcgccatcgc ctggtccaat      600
cagacctctt tcacatgcca ggatatcttt aaggagacca tgccacata ccccagctcc      660 gacgtgcctt gtgatgccac cctgacagag aagagcttcg agaccgacat gaacctgaat      720
tttcagaacc tgctggtcat cgtgctgcgg atcctgctgc tgaaggtggc cggctttaat      780
ctgctgatga cactgagact gtggtctagc                                        810

<210> SEQ ID NO 29
<211> LENGTH: 912
<212> TYPE: DNA
<213> ORGANISM: Artificial Sequence
<220> FEATURE:
<223> OTHER INFORMATION: Synthetic

<400> SEQUENCE: 29
atggcactgt gctccctgct ggccctgctg ctgggcacct ctttggcgt gaggagccag        60 accatccacc agtggcctgc cacactggtg cagcctgtgg ctccccact gtctctggag       120 tgtaccgtgg agggcacatc caacccaaat ctgtactggt ataggcaggc agcaggaaga      180
ggactgcagc tgctgttcta cagcgtgggc atcggccaga tcagtccga ggtgccacag       240 aacctgtccg cctctcggcc ccaggatagc cagttcatcc tgtctagcaa gaagctgctg      300
```

```
ctgagcgact ccggctttta cctgtgcgcc tatagccctg gcctggcctc cgatacccag      360
tatttcggcc caggcaccag gctgacagtg ctggaggacc tgcgcaacgt gacaccccct      420
aaggtgtctc tgtttgagcc tagcaaggcc gagatcgcca ataagcagaa ggccaccctg      480
gtgtgcctgg caaggggctt ctttccagat cacgtggagc tgagctggtg ggtgaacggc      540
aaggaggtgc actccggcgt gtgcaccgac ccacaggcct acaaggagag caattactcc      600
tattgtctgt cctctcggct gagagtgtcc gccacatttt ggcacaaccc aaggaatcac      660
ttccgctgcc aggtgcagtt tcacggcctg agcgaggagg ataagtggcc agagggatcc      720
cctaagccag tgacccagaa catctctgcc gaggcatggg gaagggcaga ctgtggaatc      780
acctctgcca gctatcagca gggcgtgctg agcgccacaa tcctgtacga gatcctgctg      840
ggcaaggcca ccctgtatgc cgtgctggtg tccacactgg tggtcatggc tatggtgaag      900
agaaagaact ct                                                         912

<210> SEQ ID NO 30
<211> LENGTH: 1809
<212> TYPE: DNA
<213> ORGANISM: Artificial Sequence
<220> FEATURE:
<223> OTHER INFORMATION: Synthetic

<400> SEQUENCE: 30
atggcactgc tgctgctggt gcccgtgctg gaagtgatct tcaccctggg aggaacaagg       60
gcacagtccg tgacccagct gggatctcac gtgtccgtgt ctgagggcgc cctggtgctg      120
ctgaggtgca actacagctc ctctgtgccc ccttatctgt tttggtacgt gcagtatccc      180
aatcagggcc tgcagctgct gctgaagtac accagcgccg ccacactggt gaagggcatc      240
aacggcttcg aggccgagtt taagaagtcc gagacctctt ccacctgac aaagccttct      300 gcccacatga gcgatgccgc cgagtacttt tgtgccgtga gcgaggactc caactatcag      360
ctgatctggg gcgccggcac caagctgatc atcaagcccg atatccagaa tcctgagcca      420
gccgtgtatc agctgaagga ccctcggtct caggatagca ccctgtgcct gttcacagac      480
tttgatagcc agatcaacgt gcccaagaca atggagtccg gcaccttcat cacagacaag      540
tgcgtgctgg atatgaaggc tatggacagc aagtccaacg gcgccatcgc ctggtccaat      600
cagacctctt tcacatgcca ggatatcttt aaggagacca tgccacata ccccagctcc      660 gacgtgcctt gtgatgccac cctgacagag aagagcttcg agaccgacat gaacctgaat      720
tttcagaacc tgctggtcat cgtgctgcgg atcctgctgc tgaaggtggc cggcttcaat      780
ctgctgatga ccctgagact gtggtctagc agggcaaagc ggagcggaag cggagcaaca      840 aactttccc tgctgaagca ggcaggcgac gtggaggaga tccaggacc tatggccctg      900 tgcagcctgc tggccctgct gctgggcacc ttctttggcg tgaggtccca gaccatccac      960
cagtggcctg ccacactggt gcagcctgtg ggctccccac tgtctctgga gtgtaccgtg     1020
gagggcacaa gcaacccaaa tctgtactgg tataggcagg cagcaggaag aggactgcag     1080
ctgctgttct actccgtggg catcggccag atctcctctg aggtgccaca gaacctgtcc     1140
gcctctcggc cccaggatag acagttcatc ctgagctcca gaagctgct gctgagcgac     1200 tccggctttt acctgtgcgc ctatagccct ggcctggcct ccgataccca gtatttcggc     1260
ccaggcacca ggctgacagt gctggaggac ctgcgcaacg tgacaccacc caaggtgtct     1320
ctgtttgagc ctagcaaggc cgagatcgcc aataagcaga aggccaccct ggtgtgcctg     1380
```

-continued

```
gcaaggggct tctttccaga tcacgtggag ctgtcttggt gggtgaacgg caaggaggtg      1440
cacagcggcg tgtgcaccga cccacaggcc tacaaggaga gcaattactc ctattgtctg      1500
tctagccggc tgagagtgag cgccacattt tggcacaacc caaggaatca cttccgctgc      1560
caggtgcagt ttcacggcct gagcgaggag gataagtggc cagagggatc cccaaagcca      1620
gtgacccaga acatctctgc cgaggcatgg ggaagggcag actgtggaat cacctctgcc      1680
agctatcagc agggcgtgct gtccgccaca atcctgtacg agatcctgct gggcaaggcc      1740
accctgtatg ccgtgctggt gtccacactg gtggtcatgg ctatggtgaa gagaaagaac      1800
agctgataa                                                               1809

<210> SEQ ID NO 31
<211> LENGTH: 1809
<212> TYPE: DNA
<213> ORGANISM: Artificial Sequence
<220> FEATURE:
<223> OTHER INFORMATION: Synthetic

<400> SEQUENCE: 31
atggcactgt gctccctgct ggccctgctg ctgggcacct tctttggcgt gaggagccag        60
accatccacc agtggcctgc cacactggtg cagcctgtgg gctccccact gtctctggag       120
tgtaccgtgg agggcacatc caacccaaat ctgtactggt ataggcaggc agcaggaaga       180
ggactgcagc tgctgttcta cagcgtgggc atcggccaga tcagctccga ggtgccacag       240
aacctgtccg cctctcggcc ccaggataga cagttcatcc tgtctagcaa gaagctgctg       300
ctgagcgact ccggctttta cctgtgcgcc tatagccctg cctggcctc cgatacccag       360 tatttcggcc caggcaccag gctgacagtg ctggaggacc tgcgcaacgt gacacccct       420 aaggtgtctc tgtttgagcc tagcaaggcc gagatcgcca ataagcagaa ggccaccctg       480
gtgtgcctgg caagggggct tctttccagat cacgtggagc tgagctggtg ggtgaacggc       540 aaggaggtg actccggcgt gtgcaccgac ccacaggcct acaaggagag caattactcc       600
tattgtctgt cctctcggct gagagtgtcc gccacatttt ggcacaaccc aaggaatcac       660
ttccgctgcc aggtgcagtt tcacggcctg agcgaggag ataagtggcc agagggatcc       720
cctaagccag tgacccagaa catctctgcc gaggcatggg gaagggcaga ctgtggaatc       780
acctctgcca gctatcagca gggcgtgctg agcgccacaa tcctgtacga gatcctgctg       840
ggcaaggcca ccctgtatgc cgtgctggtg tccacactgg tggtcatggc tatggtgaag       900
agaaagaact ctaggcaaa gcggagcgga tctggagcaa ccaatttcag cctgctgaag       960
caggcaggcg atgtggagga gaatccagga cctatggccc tgctgctgct ggtgcccgtg      1020
ctggaagtga tcttcaccct gggaggaaca agggcacagt ccgtgacaca gctgggatct      1080
cacgtgagcg tgtccgaggg cgccctggtg ctgctgcgct gcaactacag ctcctctgtg      1140 ccacctatc tgttctggta cgtgcagtat cccaatcagg gcctgcagct gctgctgaag      1200
tacacctccg ccgccacact ggtgaagggc atcaacggct cgaggccga gtttaagaag      1260 tctgagacca gcttccacct gacaaagcct ctgcccaca tgagcgatgc cgccgagtac      1320
ttttgtgccg tgtccgagga ctctaactat cagctgatct ggggcgccgg caccaagctg      1380
atcatcaagc ccgacatcca gaatccagag cccgccgtgt atcagctgaa ggaccctcgg      1440
agccaggatt ccaccctgtg cctgttcaca gactttgatt ctcagatcaa cgtgcccaag      1500
acaatggaga gcggcacctt catcacagac aagtgcgtgc tggatatgaa ggctatggac      1560
tctaagagca acggcgccat cgcctggtcc aatcagacct ctttcacatg ccaggatatc      1620
```

-continued

_____ tttaaggaga ccaatgccac ataccccagc tccgacgtgc cttgtgatgc caccctgaca    1680
gagaagagct cgagaccga catgaacctg aattttcaga acctgctggt catcgtgctg    1740
cggatcctgc tgctgaaggt ggccggcttt aatctgctga tgacactgag actgtggtct    1800
agctgataa                                                           1809

<210> SEQ ID NO 32
<211> LENGTH: 7319
<212> TYPE: DNA
<213> ORGANISM: Artificial Sequence
<220> FEATURE:
<223> OTHER INFORMATION: Synthetic

<400> SEQUENCE: 32
tgacatgaca agagttacta acagccctc tctccaagct cacttacagg ctctctactt      60
agtccagcac gaagtctgga gacctctggc ggcagcctac caagaacaac tggaccgacc     120
ggtggtacct cacccttacc gagtcggcga cacagtgtgg gtccgccgac accagactaa     180
gaacctagaa cctcgctgga aaggaccta cacagtcctg ctgaccaccc ccaccgccct     240
caaagtagac ggcatcgcag cttggataca cgccgcccac gtgaaggctg ccgacccccgg    300 gggtggacca tcctctagac cgccatggca ctgctgctgc tggtgcccgt gctggaagtg     360 atcttcacccc tgggaggaac aagggcacag tccgtgaccc agctgggatc tcacgtgtcc    420
gtgtctgagg gcgccctggt gctgctgagg tgcaactaca gctcctctgt gccccccttat    480 ctgtttttggt acgtgcagta tcccaatcag ggcctgcagc tgctgctgaa gtacaccagc    540
gccgccacac tggtgaaggg catcaacggc ttcgaggccg agtttaagaa gtccgagacc    600
tctttccacc tgacaaagcc ttctgcccac atgagcgatg ccgccgagta cttttgtgcc     660
gtgagcgagg actccaacta tcagctgatc tggggcgccg gcaccaagct gatcatcaag     720
cccgatatcc agaatcctga gccagccgtg tatcagctga aggaccctcg gtctcaggat    780
agcaccctgt gcctgttcac agactttgat agccagatca acgtgcccaa gacaatggag    840
tccggcacct tcatcacaga caagtgcgtg ctggatatga aggctatgga cagcaagtcc    900
aacggcgcca tcgcctggtc caatcagacc tctttcacat gccaggatat ctttaaggag    960
accaatgcca cataccccag ctccgacgtg ccttgtgatg ccaccctgac agagaagagc   1020
ttcgagaccg acatgaacct gaattttcag aacctgctgg tcatcgtgct gcggatcctg    1080
ctgctgaagg tggccggctt caatctgctg atgaccctga gactgtggtc tagcagggca    1140
aagcggagcg gaagcggagc aacaaacttt tccctgctga gcaggcagg cgacgtggag    1200 gagaatccag gacctatggc cctgtgcagc ctgctggccc tgctgctggg caccttcttt    1260
ggcgtgaggt cccagaccat ccaccagtgg cctgccacac tggtgcagcc tgtgggctcc   1320
ccactgtctc tggagtgtac cgtggagggc acaagcaacc caaatctgta ctggtatagg    1380
caggcagcag gaagaggact gcagctgctg ttctactccg tgggcatcgg ccagatctcc    1440
tctgaggtgc cacagaacct gtccgcctct cggccccagg atagacagtt catcctgagc    1500
tccaagaagc tgctgctgag cgactccggc ttttacctgt gcgcctatag ccctggcctg    1560
gcctccgata cccagtattt cggcccaggc accaggctga cagtgctgga ggacctgcgc    1620
aacgtgacac cacccaaggt gtctctgttt gagcctagca aggccgagat cgccaataag    1680
cagaaggcca ccctggtgtg cctggcaagg ggcttctttc cagatcacgt ggagctgtct    1740
tggtgggtga acggcaagga ggtgcacagc ggcgtgtgca ccgacccaca ggcctacaag    1800

-continued

```
gagagcaatt actcctattg tctgtctagc cggctgagag tgagcgccac attttggcac   1860
aacccaagga atcacttccg ctgccaggtg cagtttcacg gcctgagcga ggaggataag   1920
tggccagagg gatccccaaa gccagtgacc cagaacatct ctgccgaggc atggggaagg   1980
gcagactgtg gaatcacctc tgccagctat cagcagggcg tgctgtccgc cacaatcctg   2040
tacgagatcc tgctgggcaa ggccaccctg tatgccgtgc tggtgtccac actggtggtc   2100
atggctatgg tgaagagaaa gaacagctga taagaattct gcagtcgacg gtaccgcggg   2160
cccgggatcc gataaaataa aagattttat ttagtctcca gaaaaagggg ggaatgaaag   2220
accccacctg taggtttggc aagctagctt aagtaacgcc attttgcaag gcatggaaaa   2280
tacataactg agaatagaga agttcagatc aaggttagga acagagagac agcagaatat   2340
gggccaaaca ggatatctgt ggtaagcagt tcctgccccg gctcagggcc aagaacagat   2400
ggtccccaga tgcggtcccg ccctcagcag tttctagaga accatcagat gtttccaggg   2460
tgccccaagg acctgaaaat gaccctgtgc cttatttgaa ctaaccaatc agttcgcttc   2520
tcgcttctgt tcgcgcgctt ctgctccccg agctcaataa aagagcccac aacccctcac   2580
tcggcgcgcc agtcctccga tagactgcgt cgcccgggta cccgtgtatc caataaaccc   2640
tcttgcagtt gcatccgact tgtggtctcg ctgttccttg ggagggtctc ctctgagtga   2700
ttgactaccc gtcagcgggg gtctttcatg ggtaacagtt tcttgaagtt ggagaacaac   2760
attctgaggg taggagtcga atattaagta atcctgactc aattagccac tgttttgaat   2820
ccacatactc caatactcct gaaatccatc gatggagttc attatggaca gcgcagaaag   2880
agctggggag aattgtgaaa ttgttatccg ctcacaattc cacacaacat acgagccgga   2940
agcataaagt gtaaagcctg gggtgcctaa tgagtgagct aactcacatt aattgcgttg   3000
cgctcactgc ccgctttcca gtcgggaaac ctgtcgtgcc agctgcatta atgaatcggc   3060
caacgcgcgg ggagaggcgg tttgcgtatt gggcgctctt ccgcttcctc gctcactgac   3120
tcgctgcgct cggtcgttcg gctgcggcga gcggtatcag ctcactcaaa ggcggtaata   3180
cggttatcca cagaatcagg ggataacgca ggaaagaaca tgtgagcaaa aggccagcaa   3240
aaggccagga accgtaaaaa ggccgcgttg ctggcgtttt tccataggct ccgcccccct   3300
gacgagcatc acaaaaatcg acgctcaagt cagaggtggc gaaacccgac aggactataa   3360
agataccagg cgtttccccc tggaagctcc ctcgtgcgct ctcctgttcc gaccctgccg   3420
cttaccggat acctgtccgc ctttctccct tcgggaagcg tggcgctttc tcatagctca   3480
cgctgtaggt atctcagttc ggtgtaggtc gttcgctcca agctgggctg tgtgcacgaa   3540
ccccccgttc agcccgaccg ctgcgcctta tccggtaact atcgtcttga gtccaacccg   3600
gtaagacacg acttatcgcc actggcagca gccactggta acaggattag cagagcgagg   3660
tatgtaggcg gtgctacaga gttcttgaag tggtggccta actacggcta cactagaaga   3720
acagtatttg gtatctgcgc tctgctgaag ccagttacct tcggaaaaag agttggtagc   3780
tcttgatccg gcaaacaaac caccgctggt agcggtggtt tttttgtttg caagcagcag   3840
attacgcgca gaaaaaaagg atctcaagaa gatcctttga tcttttctac ggggtctgac   3900
gctcagtgga acgaaaactc acgttaaggg attttggtca tgagattatc aaaaaggatc   3960
ttcacctaga tccttttaaa ttaaaaatga agttttaaat caatctaaag tatatatgag   4020
taaacttggt ctgacagtta ccaatgctta atcagtgagg cacctatctc agcgatctgt   4080
ctatttcgtt catccatagt tgcctgactc cccgtcgtgt agataactac gatacgggag   4140
ggcttaccat ctggccccag tgctgcaatg ataccgcgag acccacgctc accggctcca   4200
```

-continued

```
gatttatcag caataaacca gccagccgga agggccgagc gcagaagtgg tcctgcaact   4260
ttatccgcct ccatccagtc tattaattgt tgccgggaag ctagagtaag tagttcgcca   4320
gttaatagtt tgcgcaacgt tgttgccatt gctacaggca tcgtggtgtc acgctcgtcg   4380
tttggtatgg cttcattcag ctccggttcc caacgatcaa ggcgagttac atgatccccc   4440
atgttgtgca aaaaagcggt tagctccttc ggtcctccga tcgttgtcag aagtaagttg   4500
gccgcagtgt tatcactcat ggttatggca gcactgcata attctcttac tgtcatgcca   4560
tccgtaagat gcttttctgt gactggtgag tactcaacca agtcattctg agaatagtgt   4620
atgcggcgac cgagttgctc ttgcccggcg tcaatacggg ataataccgc gccacatagc   4680
agaactttaa aagtgctcat cattggaaaa cgttcttcgg ggcgaaaact ctcaaggatc   4740
ttaccgctgt tgagatccag ttcgatgtaa cccactcgtg cacccaactg atcttcagca   4800
tcttttactt tcaccagcgt ttctgggtga gcaaaaacag gaaggcaaaa tgccgcaaaa   4860
aagggaataa gggcgacacg gaaatgttga atactcatac tcttcctttt tcaatattat   4920
tgaagcattt atcagggtta ttgtctcatg agcggataca tatttgaatg tatttagaaa   4980
aataaacaaa taggggttcc gcgcacattt ccccgaaaag tgccacctga cgtctaagaa   5040
accattatta tcatgacatt aacctataaa aataggcgta tcacgaggcc ctttcgtctc   5100
gcgcgtttcg gtgatgacgg tgaaaacctc tgacacatgc agctcccgga cacggtcaca   5160
gcttgtctgt aagcggatgc cgggagcaga caagcccgtc agggcgcgtc agcgggtgtt   5220
ggcgggtgtc ggggctggct taactatgcg gcatcagagc agattgtact gagagtgcac   5280
catatgcggt gtgaaatacc gcacagatgc gtaaggagaa aataccgcat caggcgccat   5340
tcgccattca ggctgcgcaa ctgttgggaa gggcgatcgg tgcgggcctc ttcgctatta   5400
cgccagctgg cgaaaggggg atgtgctgca aggcgattaa gttgggtaac gccagggttt   5460
tcccagtcac gacgttgtaa aacgacggcg caaggaatgg tgcatgcaag gagatggcgc   5520
ccaacagtcc cccggccacg gggcctgcca ccatacccac gccgaaacaa gcgctcatga   5580
gcccgaagtg gcgagcccga tcttccccat cggtgatgtc ggcgatatag gcgccagcaa   5640
ccgcacctgt ggcgccggtg atgccggcca cgatgcgtcc ggcgtagagg cgattagtcc   5700
aatttgttaa agacaggata tcagtggtcc aggctctagt tttgactcaa caatatcacc   5760
agctgaagcc tatagagtac gagccataga taaaataaaa gattttattt agtctccaga   5820 aaaaggggggg aatgaaagac cccacctgta ggtttggcaa gctagcttaa gtaacgccat   5880
tttgcaaggc atggaaaata cataactgag aatagaagaa ttcagatcaa ggttaggaac   5940
agagagacag cagaatatgg gccaaacagg atatctgtgg taagcagttc ctgccccggc   6000
tcagggccaa gaacagatgg tccccagatg cggtcccgcc ctcagcagtt tctagagaac   6060
catcagatgt ttccagggtg ccccaaggac ctgaaatgac cctgtgcctt atttgaacta   6120
accaatcagt tcgcttctcg cttctgttcg cgcgcttctg ctccccgagc tcaataaaag   6180
agcccacaac ccctcactcg gcgcgccagt cctccgatag actgcgtcgc ccgggtaccc   6240
gtattcccaa taaagcctct tgctgtttgc atccgaatcg tggactcgct gatccttggg   6300
agggtctcct cagattgatt gactgcccac ctcgggggtc tttcatttgg aggttccacc   6360
gagatttgga gacccctgcc cagggaccac cgacccccc gccgggaggt aagctggcca   6420
gcggtcgttt cgtgtctgtc tctgtctttg tgcgtgtttg tgccggcatc taatgtttgc   6480
gcctgcgtct gtactagtta gctaactagc tctgtatctg gcggaccgt ggtggaactg   6540
```

-continued

```
acgagttcgg aacacccggc cgcaaccctg ggagacgtcc cagggacttc gggggccgtt    6600
tttgtggccc gacctgagtc ctaaaatccc gatcgtttag gactctttgg tgcacccccc    6660
ttagaggagg gatatgtggt tctggtagga gacgagaacc taaaacagtt cccgcctccg    6720
tctgaatttt tgctttcggt ttgggaccga agccgcgccg cgcgtcttgt ctgctgcagc    6780
atcgttctgt gttgtctctg tctgactgtg tttctgtatt tgtctgaaaa tatgggcccg    6840
ggctagcctg ttaccactcc cttaagtttg accttaggtc actggaaaga tgtcgagcgg    6900
atcgctcaca accagtcggt agatgtcaag aagagacgtt gggttacctt ctgctctgca    6960
gaatggccaa cctttaacgt cggatggccg cgagacggca cctttaaccg agacctcatc    7020
acccaggtta agatcaaggt cttttcacct ggcccgcatg gacacccaga ccaggtcccc    7080
tacatcgtga cctgggaagc cttggctttt gaccccctc cctgggtcaa gcccttgta    7140 caccctaagc ctccgcctcc tcttcctcca tccgccccgt ctctcccct tgaacctcct    7200 cgttcgaccc cgcctcgatc ctcccttat ccagccctca ctccttctct aggcgccccc    7260
atatggccat atgagatctt atatgggca cccccgccc ttgtaaactt ccctgaccc     7319
```

```
<210> SEQ ID NO 33
<211> LENGTH: 7319
<212> TYPE: DNA
<213> ORGANISM: Artificial Sequence
<220> FEATURE:
<223> OTHER INFORMATION: Synthetic

<400> SEQUENCE: 33
tgacatgaca agagttacta acagccctc tctccaagct cacttacagg ctctctactt      60
agtccagcac gaagtctgga gacctctggc ggcagcctac caagaacaac tggaccgacc     120
ggtggtacct cacccttacc gagtcggcga cacagtgtgg gtccgccgac accagactaa     180
gaacctagaa cctcgctgga aaggacctta cacagtcctg ctgaccaccc ccaccgccct     240
caaagtagac ggcatcgcag cttggatacga cgccgcccac gtgaaggctg ccgaccccgg     300
gggtggacca tcctctagac cgccatggca ctgtgctccc tgctggccct gctgctgggc     360
accttctttg gcgtgaggag ccagaccatc caccagtggc ctgccacact ggtgcagcct     420
gtgggctccc cactgtctct ggagtgtacc gtggagggca catccaaccc aaatctgtac     480
tggtataggc aggcagcagg aagaggactg cagctgctgt tctacagcgt gggcatcggc     540
cagatcagct ccgaggtgcc acagaacctg tccgcctctc ggccccagga tagacagttc     600
atcctgtcta gcaagaagct gctgctgagc gactccggct tttacctgtg cgcctatagc     660
cctggcctgg cctccgatac ccagtatttc ggcccaggca ccaggctgac agtgctggag     720
gacctgcgca acgtgacacc ccctaaggtg tctctgtttg agcctagcaa ggccgagatc     780
gccaataagc agaaggccac cctggtgtgc ctggcaaggg gcttctttcc agatcacgtg     840
gagctgagct ggtgggtgaa cggcaaggag gtgcactccg gcgtgtgcac cgacccacag     900
gcctacaagg agagcaatta tctcctattgt ctgtcctctc ggctgagagt gtccgccaca     960
ttttggcaca acccaaggaa tcacttccgc tgccaggtgc agtttcacgg cctgagcgag    1020
gaggataagt ggcagagggg atccctaag ccagtgaccc agaacatctc tgccgaggca    1080
tggggaaggg cagactgtgg aatcacctct gccagctatc agcagggcgt gctgagcgcc    1140
acaatcctgt acgagatcct gctgggcaag gccaccctgt atgccgtgct ggtgtccaca    1200
ctggtggtca tggctatggt gaagagaaag aactctaggg caaagcggag cggatctgga    1260
gcaaccaatt tcagcctgct gaagcaggca ggcgatgtgg aggagaatcc aggacctatg    1320
```

-continued

```
gccctgctgc tgctggtgcc cgtgctggaa gtgatcttca ccctgggagg aacaagggca   1380
cagtccgtga cacagctggg atctcacgtg agcgtgtccg agggcgccct ggtgctgctg   1440
cgctgcaact acagctcctc tgtgccaccc tatctgttct ggtacgtgca gtatcccaat   1500
cagggcctgc agctgctgct gaagtacacc tccgccgcca cactggtgaa gggcatcaac   1560
ggcttcgagg ccgagtttaa gaagtctgag accagcttcc acctgacaaa gccttctgcc   1620
cacatgagcg atgccgccga gtactttgt gccgtgtccg aggactctaa ctatcagctg   1680
atctggggcg ccggcaccaa gctgatcatc aagcccgaca tccagaatcc agagcccgcc   1740
gtgtatcagc tgaaggaccc tcggagccag gattccaccc tgtgcctgtt cacagacttt   1800
gattctcaga tcaacgtgcc caagacaatg gagagcggca ccttcatcac agacaagtgc   1860
gtgctggata tgaaggctat ggactctaag agcaacggcg ccatcgcctg gtccaatcag   1920
acctctttca catgccagga tatctttaag gagaccaatg ccacataccc cagctccgac   1980
gtgccttgtg atgccaccct gacagagaag agcttcgaga ccgacatgaa cctgaatttt   2040
cagaacctgc tggtcatcgt gctgcggatc ctgctgctga aggtggccgg ctttaatctg   2100
ctgatgacac tgagactgtg gtctagctga taagaattct gcagtcgacg gtaccgcggg   2160
cccgggatcc gataaaataa aagattttat ttagtctcca gaaaaagggg ggaatgaaag   2220
accccacctg taggtttggc aagctagctt aagtaacgcc attttgcaag gcatggaaaa   2280
tacataactg agaatagaga agttcagatc aaggttagga acagagagac agcagaatat   2340
gggccaaaca ggatatctgt ggtaagcagt tcctgccccg gctcagggcc aagaacagat   2400
ggtccccaga tgcggtcccg ccctcagcag tttctagaga accatcagat gtttccaggg   2460
tgccccaagg acctgaaaat gaccctgtgc cttatttgaa ctaaccaatc agttcgcttc   2520
tcgcttctgt tcgcgcgctt ctgctccccg agctcaataa aagagcccac aacccctcac   2580
tcggcgcgcc agtcctccga tagactgcgt cgcccgggta cccgtgtatc caataaaccc   2640
tcttgcagtt gcatccgact tgtggtctcg ctgttccttg ggagggtctc ctctgagtga   2700
ttgactaccc gtcagcgggg gtctttcatg ggtaacagtt tcttgaagtt ggagaacaac   2760
attctgaggg taggagtcga atattaagta atcctgactc aattagccac tgtttttgaat   2820 ccacatactc caatactcct gaaatccatc gatggagttc attatggaca gcgcagaaag   2880
agctggggag aattgtgaaa ttgttatccg ctcacaattc cacacaacat acgagccgga   2940
agcataaagt gtaaagcctg gggtgcctaa tgagtgagct aactcacatt aattgcgttg   3000
cgctcactgc ccgctttcca gtcgggaaac ctgtcgtgcc agctgcatta atgaatcggc   3060
caacgcgcgg ggagaggcgg tttgcgtatt gggcgctctt ccgcttcctc gctcactgac   3120
tcgctgcgct cggtcgttcg gctgcggcga gcggtatcag ctcactcaaa ggcggtaata   3180
cggttatcca cagaatcagg ggataacgca ggaaagaaca tgtgagcaaa aggccagcaa   3240
aaggccagga accgtaaaaa ggccgcgttg ctggcgtttt tccataggct ccgcccccct   3300
gacgagcatc acaaaaatcg acgctcaagt cagaggtggc gaaacccgac aggactataa   3360
agataccagg cgtttccccc tggaagctcc ctcgtgcgct ctcctgttcc gaccctgccg   3420
cttaccggat acctgtccgc ctttctccct tcgggaagcg tggcgctttc tcatagctca   3480
cgctgtaggt atctcagttc ggtgtaggtc gttcgctcca agctgggctg tgtgcacgaa   3540 cccccgttc agcccgaccg ctgcgcctta tccggtaact atcgtcttga gtccaacccg   3600
gtaagacacg acttatcgcc actggcagca gccactggta acaggattag cagagcgagg   3660
```

-continued

```
tatgtaggcg gtgctacaga gttcttgaag tggtggccta actacggcta cactagaaga   3720
acagtatttg gtatctgcgc tctgctgaag ccagttacct tcggaaaaag agttggtagc   3780
tcttgatccg gcaaacaaac caccgctggt agcggtggtt tttttgtttg caagcagcag   3840
attacgcgca gaaaaaaagg atctcaagaa gatcctttga tcttttctac ggggtctgac   3900
gctcagtgga acgaaaactc acgttaaggg attttggtca tgagattatc aaaaaggatc   3960
ttcacctaga tccttttaaa ttaaaaatga agttttaaat caatctaaag tatatatgag   4020
taaacttggt ctgacagtta ccaatgctta atcagtgagg cacctatctc agcgatctgt   4080
ctatttcgtt catccatagt tgcctgactc cccgtcgtgt agataactac gatacgggag   4140
ggcttaccat ctggccccag tgctgcaatg ataccgcgag acccacgctc accggctcca   4200
gatttatcag caataaacca gccagccgga agggccgagc gcagaagtgg tcctgcaact   4260
ttatccgcct ccatccagtc tattaattgt tgccgggaag ctagagtaag tagttcgcca   4320
gttaatagtt tgcgcaacgt tgttgccatt gctacaggca tcgtggtgtc acgctcgtcg   4380
tttggtatgg cttcattcag ctccggttcc caacgatcaa ggcgagttac atgatccccc   4440
atgttgtgca aaaaagcggt tagctccttc ggtcctccga tcgttgtcag aagtaagttg   4500
gccgcagtgt tatcactcat ggttatggca gcactgcata attctcttac tgtcatgcca   4560
tccgtaagat gcttttctgt gactggtgag tactcaacca agtcattctg agaatagtgt   4620
atgcggcgac cgagttgctc ttgcccggcg tcaatacggg ataataccgc gccacatagc   4680
agaactttaa aagtgctcat cattggaaaa cgttcttcgg ggcgaaaact ctcaaggatc   4740
ttaccgctgt tgagatccag ttcgatgtaa cccactcgtg cacccaactg atcttcagca   4800
tcttttactt tcaccagcgt ttctgggtga gcaaaaacag gaaggcaaaa tgccgcaaaa   4860
aagggaataa gggcgacacg gaaatgttga atactcatac tcttcctttt tcaatattat   4920
tgaagcattt atcagggtta ttgtctcatg agcggataca tatttgaatg tatttagaaa   4980
aataaacaaa tagggggttcc gcgcacattt ccccgaaaag tgccacctga cgtctaagaa   5040
accattatta tcatgacatt aacctataaa aataggcgta tcacgaggcc ctttcgtctc   5100
gcgcgtttcg gtgatgacgg tgaaaacctc tgacacatgc agctcccgga cacggtcaca   5160
gcttgtctgt aagcggatgc cgggagcaga caagcccgtc agggcgcgtc agcgggtgtt   5220
ggcgggtgtc ggggctggct taactatgcg gcatcagagc agattgtact gagagtgcac   5280
catatgcggt gtgaaatacc gcacagatgc gtaaggagaa aataccgcat caggcgccat   5340
tcgccattca ggctgcgcaa ctgttgggaa gggcgatcgg tgcgggcctc ttcgctatta   5400
cgccagctgg cgaaaggggg atgtgctgca aggcgattaa gttgggtaac gccagggttt   5460
tcccagtcac gacgttgtaa aacgacggcg caaggaatgg tgcatgcaag gagatggcgc   5520
ccaacagtcc cccggccacg gggcctgcca ccatacccac gccgaaacaa gcgctcatga   5580
gcccgaagtg gcgagcccga tcttccccat cggtgatgtc ggcgatatag cgcgcagcaa   5640
ccgcacctgt ggcgccggtg atgccggcca cgatgcgtcc ggcgtagagg cgattagtcc   5700
aatttgttaa agacaggata tcagtggtcc aggctctagt tttgactcaa caatatcacc   5760
agctgaagcc tatagagtac gagccataga taaaataaaa gattttattt agtctccaga   5820 aaaaggggggg aatgaaagac cccacctgta ggtttggcaa gctagcttaa gtaacgccat   5880
tttgcaaggc atggaaaata cataactgag aatagagaag ttcagatcaa ggttaggaac   5940
agagagacag cagaatatgg gccaaacagg atatctgtgg taagcagttc ctgccccggc   6000
tcagggccaa gaacagatgg tccccagatg cggtcccgcc ctcagcagtt tctagagaac   6060
```

```
catcagatgt ttccagggtg ccccaaggac ctgaaatgac cctgtgcctt atttgaacta    6120
accaatcagt tcgcttctcg cttctgttcg cgcgcttctg ctccccgagc tcaataaaag    6180
agcccacaac ccctcactcg gcgcgccagt cctccgatag actgcgtcgc ccgggtaccc    6240
gtattcccaa taaagcctct tgctgtttgc atccgaatcg tggactcgct gatccttggg    6300
agggtctcct cagattgatt gactgcccac ctcgggggtc tttcatttgg aggttccacc    6360
gagatttgga gacccctgcc cagggaccac cgaccccccc gccgggaggt aagctggcca    6420
gcggtcgttt cgtgtctgtc tctgtctttg tgcgtgtttg tgccggcatc taatgtttgc    6480
gcctgcgtct gtactagtta gctaactagc tctgtatctg cgcgaccgt ggtggaactg     6540 acgagttcgg aacacccggc cgcaaccctg ggagacgtcc cagggacttc gggggccgtt    6600
tttgtggccc gacctgagtc ctaaaatccc gatcgtttag gactctttgg tgcacccccc    6660
ttagaggagg gatatgtggt tctggtagga gacgagaacc taaaacagtt cccgcctccg    6720
tctgaatttt tgctttcggt ttgggaccga agccgcgccg cgcgtcttgt ctgctgcagc    6780
atcgttctgt gttgtctctg tctgactgtg tttctgtatt tgtctgaaaa tatgggcccg    6840
ggctagcctg ttaccactcc cttaagtttg accttaggtc actggaaaga tgtcgagcgg    6900
atcgctcaca accagtcggt agatgtcaag aagagacgtt gggttacctt ctgctctgca    6960
gaatggccaa cctttaacgt cggatggccg cgagacggca cctttaaccg agacctcatc    7020
acccaggtta agatcaaggt cttttcacct ggcccgcatg gacacccaga ccaggtcccc    7080
tacatcgtga cctgggaagc cttggctttt gacccccctc cctgggtcaa gccctttgta    7140
caccctaagc ctccgcctcc tcttcctcca tccgccccgt ctctcccct tgaacctcct     7200 cgttcgaccc cgcctcgatc ctcccttat ccagccctca ctccttctct aggcgcccc     7260 atatggccat atgagatctt atatggggca cccccgcccc ttgtaaactt ccctgaccc     7319
```

<210> SEQ ID NO 34
<211> LENGTH: 25
<212> TYPE: PRT
<213> ORGANISM: Homo sapiens

<400> SEQUENCE: 34

```
Pro Glu Gly Glu Lys Val Lys Ile Pro Val Ala Ile Lys Glu Leu Arg
1               5                   10                  15

Glu Ala Thr Ser Pro Lys Ala Asn Lys
            20                  25
```

<210> SEQ ID NO 35
<211> LENGTH: 25
<212> TYPE: PRT
<213> ORGANISM: Homo sapiens

<400> SEQUENCE: 35

```
Pro Glu Gly Glu Lys Val Lys Ile Pro Val Ala Ile Lys Thr Ser Pro
1               5                   10                  15

Lys Ala Asn Lys Glu Ile Leu Asp Glu
            20                  25
```

<210> SEQ ID NO 36
<211> LENGTH: 13
<212> TYPE: PRT
<213> ORGANISM: Homo sapiens

<400> SEQUENCE: 36

```
Ala Ile Lys Thr Ser Pro Lys Ala Asn Lys Glu Ile Leu
1               5               10

<210> SEQ ID NO 37
<211> LENGTH: 12
<212> TYPE: PRT
<213> ORGANISM: Homo sapiens

<400> SEQUENCE: 37

Ala Ile Lys Thr Ser Pro Lys Ala Asn Lys Glu Ile
1               5               10

<210> SEQ ID NO 38
<211> LENGTH: 12
<212> TYPE: PRT
<213> ORGANISM: Homo sapiens

<400> SEQUENCE: 38

Ile Lys Thr Ser Pro Lys Ala Asn Lys Glu Ile Leu
1               5               10

<210> SEQ ID NO 39
<211> LENGTH: 11
<212> TYPE: PRT
<213> ORGANISM: Homo sapiens

<400> SEQUENCE: 39

Ile Lys Thr Ser Pro Lys Ala Asn Lys Glu Ile
1               5               10

<210> SEQ ID NO 40
<211> LENGTH: 23
<212> TYPE: PRT
<213> ORGANISM: Homo sapiens

<400> SEQUENCE: 40

Gly Glu Lys Val Lys Ile Pro Val Ala Ile Lys Thr Ser Pro Lys Ala
1               5               10              15

Asn Lys Glu Ile Leu Asp Glu
            20

<210> SEQ ID NO 41
<211> LENGTH: 21
<212> TYPE: PRT
<213> ORGANISM: Homo sapiens

<400> SEQUENCE: 41

Lys Val Lys Ile Pro Val Ala Ile Lys Thr Ser Pro Lys Ala Asn Lys
1               5               10              15

Glu Ile Leu Asp Glu
            20

<210> SEQ ID NO 42
<211> LENGTH: 19
<212> TYPE: PRT
<213> ORGANISM: Homo sapiens

<400> SEQUENCE: 42

Lys Ile Pro Val Ala Ile Lys Thr Ser Pro Lys Ala Asn Lys Glu Ile
1               5               10              15

Leu Asp Glu

<210> SEQ ID NO 43
```

-continued

```
<211> LENGTH: 17
<212> TYPE: PRT
<213> ORGANISM: Homo sapiens

<400> SEQUENCE: 43

Pro Val Ala Ile Lys Thr Ser Pro Lys Ala Asn Lys Glu Ile Leu Asp
1               5                   10                  15

Glu

<210> SEQ ID NO 44
<211> LENGTH: 15
<212> TYPE: PRT
<213> ORGANISM: Homo sapiens

<400> SEQUENCE: 44

Ala Ile Lys Thr Ser Pro Lys Ala Asn Lys Glu Ile Leu Asp Glu
1               5                   10                  15

<210> SEQ ID NO 45
<211> LENGTH: 13
<212> TYPE: PRT
<213> ORGANISM: Homo sapiens

<400> SEQUENCE: 45

Lys Thr Ser Pro Lys Ala Asn Lys Glu Ile Leu Asp Glu
1               5                   10

<210> SEQ ID NO 46
<211> LENGTH: 23
<212> TYPE: PRT
<213> ORGANISM: Homo sapiens

<400> SEQUENCE: 46

Pro Glu Gly Glu Lys Val Lys Ile Pro Val Ala Ile Lys Thr Ser Pro
1               5                   10                  15

Lys Ala Asn Lys Glu Ile Leu
            20

<210> SEQ ID NO 47
<211> LENGTH: 21
<212> TYPE: PRT
<213> ORGANISM: Homo sapiens

<400> SEQUENCE: 47

Pro Glu Gly Glu Lys Val Lys Ile Pro Val Ala Ile Lys Thr Ser Pro
1               5                   10                  15

Lys Ala Asn Lys Glu
            20

<210> SEQ ID NO 48
<211> LENGTH: 19
<212> TYPE: PRT
<213> ORGANISM: Homo sapiens

<400> SEQUENCE: 48

Pro Glu Gly Glu Lys Val Lys Ile Pro Val Ala Ile Lys Thr Ser Pro
1               5                   10                  15

Lys Ala Asn

<210> SEQ ID NO 49
<211> LENGTH: 17
<212> TYPE: PRT
<213> ORGANISM: Homo sapiens
```

-continued

```
<400> SEQUENCE: 49

Pro Glu Gly Glu Lys Val Lys Ile Pro Val Ala Ile Lys Thr Ser Pro
1               5                  10                  15

Lys

<210> SEQ ID NO 50
<211> LENGTH: 15
<212> TYPE: PRT
<213> ORGANISM: Homo sapiens

<400> SEQUENCE: 50

Pro Glu Gly Glu Lys Val Lys Ile Pro Val Ala Ile Lys Thr Ser
1               5                  10                  15

<210> SEQ ID NO 51
<211> LENGTH: 5
<212> TYPE: PRT
<213> ORGANISM: Homo sapiens

<400> SEQUENCE: 51

Glu Leu Arg Glu Ala
1               5
```